(12) United States Patent
Erdman et al.

(10) Patent No.: US 11,166,636 B2
(45) Date of Patent: Nov. 9, 2021

(54) BREATH SAMPLING MASK AND SYSTEM

(71) Applicants: REGENTS OF THE UNIVERSITY OF MINNESOTA, Minneapolis, MN (US); Boston Scientific Scimed, Inc., Maple Grove, MN (US)

(72) Inventors: Arthur Guy Erdman, New Brighton, MN (US); Gregory J. Sherwood, North Oaks, MN (US); Gregory Kermit Peterson, North Oaks, MN (US); Justin Theodore Nelson, Minneapolis, MN (US); Michael Mathias Freking, Arden Hills, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 279 days.

(21) Appl. No.: 16/280,644

(22) Filed: Feb. 20, 2019

(65) Prior Publication Data

US 2019/0254538 A1    Aug. 22, 2019

Related U.S. Application Data

(60) Provisional application No. 62/632,552, filed on Feb. 20, 2018.

(51) Int. Cl.
*A61B 5/08* (2006.01)
*A61B 5/097* (2006.01)
(Continued)

(52) U.S. Cl.
CPC ........ *A61B 5/02055* (2013.01); *A61B 5/6803* (2013.01); *A61B 5/021* (2013.01);
(Continued)

(58) Field of Classification Search
CPC ................................ A61B 5/082; A61B 5/097
See application file for complete search history.

(56) References Cited

U.S. PATENT DOCUMENTS

| 5,704,368 A | 1/1998 | Asano et al. |
| 5,834,626 A | 11/1998 | De Castro et al. |

(Continued)

FOREIGN PATENT DOCUMENTS

| CN | 1301342 | 6/2001 |
| CN | 107076693 | 9/2017 |

(Continued)

OTHER PUBLICATIONS

Magera, Mark J. et al., "Methylmalonic Acid Measured in Plasma and Urine by Stable-Isotope Dilution and Electrospray Tandem Mass Spectrometry," Clin Chem. Nov. 2000;46(11):1804-10 (7 pages).

(Continued)

*Primary Examiner* — Thaddeus B Cox
(74) *Attorney, Agent, or Firm* — Pauly, DeVries Smith & Deffner LLC

(57) ABSTRACT

Embodiments herein include a breath sampling mask, systems, and related methods. In an embodiment, a breath sensing system is included. The breath sensing system can include a breath sampling mask. The breath sampling mask can include a mask housing configured to cover a portion of the face of a patient. The mask housing can define a breath receiving chamber. The breath sampling mask can include a chemical sensor element in fluid communication with the breath sampling mask, where the chemical sensor element can include a plurality of discrete binding detectors. The chemical sensor element can interface with a breath sample collected through the breath sampling mask. Other embodiments are also included herein.

14 Claims, 15 Drawing Sheets

(51) Int. Cl.
*A61B 5/0205* (2006.01)
*A61B 5/00* (2006.01)
*A61B 5/021* (2006.01)
*A61B 5/024* (2006.01)

(52) U.S. Cl.
CPC .......... *A61B 5/02438* (2013.01); *A61B 5/082* (2013.01); *A61B 5/097* (2013.01); *A61B 2560/0242* (2013.01)

(56) References Cited

U.S. PATENT DOCUMENTS

| | | |
|---|---|---|
| 6,085,576 A | 7/2000 | Sunshine et al. |
| 6,149,624 A | 11/2000 | Mcshane |
| 6,192,168 B1 | 2/2001 | Feldstein et al. |
| 6,248,078 B1 | 6/2001 | Risby et al. |
| 6,312,390 B1 | 11/2001 | Phillips et al. |
| 6,480,734 B1 | 11/2002 | Zhang et al. |
| 6,599,253 B1 | 7/2003 | Baum et al. |
| 6,712,770 B2 | 3/2004 | Lin et al. |
| 6,726,637 B2 | 4/2004 | Phillips et al. |
| 6,781,690 B2 | 8/2004 | Armstrong et al. |
| 6,955,652 B1 | 10/2005 | Baum et al. |
| 6,978,182 B2 | 12/2005 | Mazar et al. |
| 7,032,431 B2 | 4/2006 | Baum et al. |
| 7,123,359 B2 | 10/2006 | Armstrong et al. |
| 7,177,686 B2 | 2/2007 | Turcott et al. |
| 7,426,848 B1 | 9/2008 | Li et al. |
| 7,459,312 B2 | 12/2008 | Chen et al. |
| 7,704,214 B2 | 4/2010 | Meixner et al. |
| 7,809,441 B2 | 10/2010 | Kane et al. |
| 7,871,572 B2 | 1/2011 | Yang et al. |
| 7,972,277 B2 | 7/2011 | Oki et al. |
| 7,992,422 B2 | 8/2011 | Leddy et al. |
| 8,043,860 B2 | 10/2011 | Leznoff et al. |
| 8,080,206 B2 | 12/2011 | Leddy et al. |
| 8,124,419 B2 | 2/2012 | Grigorian et al. |
| 8,153,439 B2 | 4/2012 | Zamborini et al. |
| 8,154,093 B2 | 4/2012 | Passmore et al. |
| 8,157,730 B2 | 4/2012 | Tucker et al. |
| 8,222,041 B2 | 7/2012 | Pearton et al. |
| 8,366,630 B2 | 2/2013 | Haick et al. |
| 8,481,324 B2 | 7/2013 | Nakhoul et al. |
| 8,494,606 B2 | 7/2013 | Debreczeny et al. |
| 8,529,459 B2 | 9/2013 | Stahl, Jr. et al. |
| 8,597,953 B2 | 12/2013 | Haick et al. |
| 8,747,325 B2 | 6/2014 | Bacal et al. |
| 8,828,713 B2 | 9/2014 | Ren et al. |
| 8,835,984 B2 | 9/2014 | Ren et al. |
| 8,848,189 B2 | 9/2014 | Goldshtein et al. |
| 8,955,367 B2 | 2/2015 | Gouma et al. |
| 9,011,779 B1 | 4/2015 | Anglin, Jr. et al. |
| 9,029,168 B2 | 5/2015 | Mannoor et al. |
| 9,103,775 B2 | 8/2015 | Bradley et al. |
| 9,147,851 B1 | 9/2015 | Bartsch et al. |
| 9,315,848 B2 | 4/2016 | Haick et al. |
| 9,316,637 B2 | 4/2016 | Ren et al. |
| 9,324,825 B2 | 4/2016 | Ravesi et al. |
| 9,366,664 B2 | 6/2016 | Anglin, Jr. et al. |
| 9,513,244 B2 | 12/2016 | Koester |
| 9,618,476 B2 | 4/2017 | Goldsmith |
| 9,643,186 B1* | 5/2017 | Ahmad .................. B01L 3/561 |
| 9,765,395 B2 | 9/2017 | Goldsmith |
| 10,191,005 B2 | 1/2019 | Koester |
| 2002/0123749 A1 | 9/2002 | Jain et al. |
| 2002/0142477 A1 | 10/2002 | Lewis et al. |
| 2003/0051733 A1 | 3/2003 | Kotmel et al. |
| 2003/0060726 A1* | 3/2003 | Lin ....................... A61B 5/201 600/532 |
| 2003/0176804 A1* | 9/2003 | Melker ................. A61M 16/01 600/532 |
| 2006/0130557 A1 | 6/2006 | Leddy et al. |
| 2006/0263255 A1 | 11/2006 | Han et al. |
| 2006/0270940 A1 | 11/2006 | Tsukashima et al. |
| 2007/0048181 A1 | 3/2007 | Chang et al. |
| 2007/0083094 A1 | 4/2007 | Colburn et al. |
| 2007/0167853 A1 | 7/2007 | Melker et al. |
| 2007/0229818 A1 | 10/2007 | Duan et al. |
| 2008/0021339 A1 | 1/2008 | Gabriel et al. |
| 2008/0146890 A1 | 6/2008 | Leboeuf et al. |
| 2008/0183910 A1 | 7/2008 | Natoli et al. |
| 2008/0317636 A1 | 12/2008 | Brahim et al. |
| 2009/0054799 A1 | 2/2009 | Vrtis et al. |
| 2009/0112115 A1 | 4/2009 | Huang et al. |
| 2010/0024533 A1 | 2/2010 | Kimura et al. |
| 2010/0085067 A1 | 4/2010 | Gabriel et al. |
| 2010/0137733 A1 | 6/2010 | Wang et al. |
| 2010/0188069 A1 | 7/2010 | Ren et al. |
| 2010/0198521 A1 | 8/2010 | Haick et al. |
| 2010/0216175 A1 | 8/2010 | Melker et al. |
| 2010/0273665 A1 | 10/2010 | Haick et al. |
| 2011/0015872 A1 | 1/2011 | Haick et al. |
| 2011/0017587 A1 | 1/2011 | Zhamu et al. |
| 2011/0143962 A1 | 6/2011 | Chaubron et al. |
| 2011/0269632 A1 | 11/2011 | Haick et al. |
| 2011/0283770 A1 | 11/2011 | Hok et al. |
| 2012/0111093 A1 | 5/2012 | Brahim et al. |
| 2012/0126111 A1 | 5/2012 | Chaubron et al. |
| 2012/0156099 A1 | 6/2012 | Zhong et al. |
| 2012/0166095 A1 | 6/2012 | Potyrailo et al. |
| 2012/0203081 A1 | 8/2012 | Leboeuf et al. |
| 2012/0226111 A1 | 9/2012 | Leboeuf et al. |
| 2012/0226112 A1 | 9/2012 | Leboeuf et al. |
| 2012/0245434 A1 | 9/2012 | Haick et al. |
| 2012/0245854 A1 | 9/2012 | Haick et al. |
| 2012/0326092 A1 | 12/2012 | Haick et al. |
| 2013/0006068 A1* | 1/2013 | Gemer ............... A61B 10/0051 600/314 |
| 2013/0034190 A1 | 2/2013 | Tan et al. |
| 2013/0034910 A1 | 2/2013 | Haick et al. |
| 2013/0059758 A1 | 3/2013 | Haick et al. |
| 2013/0102018 A1 | 4/2013 | Schentag et al. |
| 2013/0143247 A1 | 6/2013 | Haick et al. |
| 2013/0150261 A1 | 6/2013 | Haick et al. |
| 2013/0171733 A1 | 7/2013 | Haick et al. |
| 2013/0211207 A1 | 8/2013 | Joseph et al. |
| 2013/0211852 A1 | 8/2013 | Roizen et al. |
| 2013/0236981 A1 | 9/2013 | Haick et al. |
| 2013/0253358 A1 | 9/2013 | Phillips et al. |
| 2013/0289368 A1 | 10/2013 | Covington et al. |
| 2013/0334579 A1 | 12/2013 | Accardi et al. |
| 2014/0018691 A1 | 1/2014 | Mcneill et al. |
| 2014/0051956 A1 | 2/2014 | Dalene et al. |
| 2014/0145735 A1 | 5/2014 | Koester et al. |
| 2014/0275597 A1 | 9/2014 | Zhang et al. |
| 2014/0294675 A1 | 10/2014 | Melker et al. |
| 2014/0364758 A1* | 12/2014 | Schindhelm ...... A61M 16/0666 600/531 |
| 2015/0013429 A1 | 1/2015 | Atkin et al. |
| 2015/0038378 A1 | 2/2015 | Cheng et al. |
| 2015/0044710 A1 | 2/2015 | Dasgupta et al. |
| 2015/0065365 A1 | 3/2015 | Ahmad |
| 2015/0217075 A1* | 8/2015 | Nair ........................ A61B 1/01 600/531 |
| 2015/0257676 A1 | 9/2015 | Fries |
| 2015/0307936 A1 | 10/2015 | Goldsmith |
| 2015/0309018 A1 | 10/2015 | Goldsmith |
| 2015/0335266 A1 | 11/2015 | Cormier |
| 2015/0338390 A1 | 11/2015 | Anglin et al. |
| 2016/0025675 A1 | 1/2016 | Goldsmith |
| 2016/0054312 A1 | 2/2016 | Goldsmith |
| 2016/0109440 A1* | 4/2016 | Sherwood ............ G01N 27/227 436/501 |
| 2016/0116431 A1 | 4/2016 | Accardi et al. |
| 2016/0231309 A1 | 8/2016 | Ahmad et al. |
| 2016/0296168 A1* | 10/2016 | Abreu ................. A61B 5/6803 |
| 2017/0014043 A1 | 1/2017 | Mcdonnell |
| 2017/0042435 A1 | 2/2017 | Vermeulen et al. |
| 2017/0053068 A1 | 2/2017 | Pillai et al. |
| 2017/0251952 A1 | 9/2017 | Harshman et al. |
| 2017/0254817 A1 | 9/2017 | Grafman et al. |
| 2017/0303822 A1* | 10/2017 | Allsworth .......... B01D 46/0028 |
| 2017/0307562 A1 | 10/2017 | Goldsmith |
| 2017/0307576 A1* | 10/2017 | Anglin, Jr. ......... G01N 33/0059 |

(56) References Cited

U.S. PATENT DOCUMENTS

| | | |
|---|---|---|
| 2017/0360337 A1 | 12/2017 | Sherwood et al. |
| 2017/0361599 A1 | 12/2017 | Lerner et al. |
| 2017/0365474 A1 | 12/2017 | Pan et al. |
| 2017/0365477 A1 | 12/2017 | Pan et al. |
| 2017/0365562 A1 | 12/2017 | Pan et al. |
| 2018/0037952 A1 | 2/2018 | Goldsmith |
| 2018/0037985 A1 | 2/2018 | Myers et al. |
| 2018/0110444 A1 | 4/2018 | Sherwood et al. |
| 2018/0228400 A1* | 8/2018 | Baba .............. A61M 16/0605 |
| 2018/0336970 A1 | 11/2018 | Sherwood et al. |
| 2019/0025237 A1 | 1/2019 | Kelly et al. |
| 2019/0365283 A1* | 12/2019 | Chou ................. G01N 1/30 |
| 2020/0124588 A1 | 4/2020 | Peterson et al. |
| 2020/0337566 A1 | 10/2020 | Peterson et al. |

FOREIGN PATENT DOCUMENTS

| | | |
|---|---|---|
| CN | 109270130 | 1/2019 |
| CN | 109310326 | 2/2019 |
| EP | 1764153 | 3/2007 |
| EP | 1806414 | 7/2007 |
| EP | 3093653 | 11/2016 |
| EP | 3210007 | 8/2017 |
| EP | 3431977 | 1/2019 |
| EP | 3439544 | 2/2019 |
| GB | 2523180 | 8/2015 |
| JP | 2011102747 | 5/2011 |
| JP | 2019020415 | 2/2019 |
| WO | 9947905 | 9/1999 |
| WO | 2001070114 | 9/2001 |
| WO | 2008088780 | 7/2008 |
| WO | 2009135070 | 11/2009 |
| WO | 2013090999 | 6/2013 |
| WO | 2013095730 | 6/2013 |
| WO | 2013189502 | 12/2013 |
| WO | 2015191558 | 12/2015 |
| WO | 2016064740 | 4/2016 |
| WO | 2016105464 | 6/2016 |
| WO | 2017218464 | 12/2017 |
| WO | 2018075731 | 4/2018 |
| WO | 2018213564 | 11/2018 |

OTHER PUBLICATIONS

Murphy, Michael P. et al., "Krebs Cycle Reimagined: The Emerging Roles of Succinate and Itaconate as Signal Transducers," Cell, vol. 174, Issue 4, Aug. 9, 2018, pp. 780-784 (5 pages).
International Search Report and Written Opinion for PCT Application No. PCT/US2019/056766 dated Mar. 17, 2020.
"10 Leading Causes of Death, United States," (NCIPC) NCflPaC. Web-based Injury Statistics Query and Reporting System. https://webappa.cdc.gov/sasweb/ncipc/leadcause.html, as available on Feb. 23, 2018 (3 pages).
Banoei, Mohammad M. et al., "Metabolomics and Biomarker Discovery in Traumatic Brain Injury," Journal of Neurotrauma, vol. 35, No. 16, Mar. 2018 (59 pages).
Chinopoulos, Christos "Which way Does the Citric Acid Cycle Turn During Hypoxia? The Critical Role of α-Ketoglutarate Dehydrogenase Complex," Journal of Neuroscience Research 91:1030-1043 (2013), 14 pages.
Chouchani, Edward T. et al., "Ischaemic Accumulation of Succinate Controls Reperfusion Injury Through Mitochondrial ROS," Nature. 2014; 515 (7527):431-435 (author manuscript), 29 pages.
D'alessandro, Angelo et al., "Early Hemorrhage Triggers Metabolic Responses That Build Up During Prolonged Shock," Am J Physiol Regul Integr Comp Physiol 308: R1034-R1044, 2015 (11 pages).
D'alessandro, Angelo et al., "Plasma Succinate is a Predictor of Mortality in Critically Injured Patients," Journal of Trauma and Acute Care Surgery. 2017;83(3):491-495, Author manuscript (9 pages).
D'alessandro, Angelo et al., "Trauma/Hemorrhagic Shock Instigates Aberrant Metabolic Flux Through Glycolytic Pathways, as Revealed by Preliminary C-glucose Labeling Metabolomics," Journal of Translational Medicine 2015;13(1): 253 (14 pages).
El Sayad, Mohamed et al., "Recent Advances of Hemorrhage Management in Severe Trauma," Emergency Medicine International, vol. 2014, Article ID 635956 (5 pages).
Goolsby, Craig et al., "Just-in-Time to Save Lives: A Pilot Study of Layperson Tourniquet Application," Academic Emergency Medicine, 2015;22(9):1113-1117 (5 pages).
Gutierrez, Guillermo et al., "Clinical Review: Hemorrhagic Shock," Critical Care 2004, 8:373-381 (9 pages).
Hill, Lisa J. et al., "Cystain D (CST5): An Ultra-Early Inflammatory Biomarker of Traumatic Brain Injury," Sci Rep. Jul. 10, 2017;7(1):5002 (10 pages).
Howard, Jt et al., "Reexamination of a Battlefield Trauma Golden Hour Policy," Journal of Trauma and Acute Care Surgery 2018;84(1):11-18, Abstract only (2 pages).
Kauvar, David S. et al., "Impact of Hemorrhage on Trauma Outcome: An Overview of Epidemiology, Clinical Presentations, and Therapeutic Considerations," Journal of Trauma and Acute Care Surgery, 2006;60(6): S3-S11 (9 pages).
Kotwal, Russ S. et al., "Eliminating Preventable Death on the Battlefield," Archives of Surgery 2011;146(12): 1350-1358 (9 pages).
Krausz, Michael M. "Initial Resuscitation of Hemorrhagic Shock," World Journal of Emergency Surgery 2006, 1:14 (5 pages).
Lexcen, D. R. et al., "Metabolomics Classifies Phase of Care and Identifies Risk for Mortality in a Porcine Model of Multiple Injuries and Hemorrhagic Shock," Journal of Trauma and Acute Care Surgery 2012;73(2):5147-5155, Abstract only (2 pages).
Lusczek, Elizabeth R. et al., "Assessment of Key Plasma Metabolites in Combat Casualties," Journal of Trauma and Acute Care Surgery. 2017;82(2):309-316 (8 pages).
Partial File History for U.S. Appl. No. 14/883,895, filed Nov. 15, 2015 to Feb. 5, 2020 (284 pages).
"Researchers Identify Inflammatory Biomarkers Indicating Brain Injury," University of Birmingham, posted Jul. 10, 2017 <https://www.birmingham.ac.uk/news/latest/2017/07/researchers-identify-inflammatory-biomarkers-indicating-brain-injury.aspx> (4 pages).
Russo, Matthew V. et al., "Inflammatory Neuroprotection Following Traumatic Brain Injury," Science. Aug. 19, 2016;353(6301):783-5 (4 pages).
Slaughter, Anne L. et al., "Glutamine Metabolism Drives Succinate Accumulation in Plasma and the Lung During Hemorrhagic Shock," Journal of Trauma and Acute Care Surgery. 2016;81(6):1012-1019 (8 pages).
Stewart, Ian J. et al., "The Potential Utility of Urinary Biomarkers for Risk Prediction in Combat Casualties: A Prospective Observational Cohort Study," Critical Care 2015;19(1):252 (8 pages).
Witowski, Nancy E. et al., "Metabolomic Analysis of Survival in Carbohydrate Pre-Fed Pigs Subjected to Shock and Polytrauma," Molecular BioSystems Apr. 26, 2016; 12(5), 34 pages.
Woodcock, Thomas et al., "The Role of Markers of Inflammation in Traumatic Brain Injury," Front Neurol. Mar. 4, 2013;4:18 (18 pages).
Chen, Liangyou et al., "Diagnosis of Hemorrhage in a Prehospital Trauma Population Using Linear and Nonlinear Multiparameter Analysis of Vital Signs," 2007 Annual International Conference of the IEEE Engineering and Medicine and Biology Society, Aug. 22, 2007 (4 pages).
International Search Report and Written Opinion for PCT Application No. PCT/US2020/030223 dated Jul. 27, 2020 (17 pages).
Rassaei, Liza et al., "Lactate Biosensors: Current Status and Outlook," Anal Bioanal Chem (2014) 406:123-137 (16 pages).
Umbrello, Michele et al., "The Key Role of Nitric Oxide in Hypoxia: Hypoxic Vasodilation and Energy Supply-Demand Matching," Antioxidants and Redox Signaling, vol. 19, No. 14, Nov. 10, 2013 (22 pages).
International Preliminary Report on Patentability for PCT Application No. PCT/US2019/081744 dated Sep. 3, 2020 (11 pages).
Arasaradnam, R. P. et al., "Review Article: Next Generation Diagnostic Modalities in Gastroenterology—Gas Phase Volatile compound biomarker detection," Alimentary Pharmacology and Therapeutics 2014; 39: 780-789 (10 pages).

(56) References Cited

OTHER PUBLICATIONS

Boots, Agnes W. et al., "The Versatile Use of Exhaled Volatile Organic Compounds in Human Health and Disease," J. Breath Res. 6 (2012) 027108 (21 pages).

"Communication Pursuant to Article 94(3) EPC," for European Patent Application No. 18180455.0 dated Feb. 11, 2019 (6 pages).

"Communication Pursuant to Rules 161(1) and 162 EPC," for European Patent Application No. 15790739.5 dated Jun. 1, 2017 (2 pages).

Deen, David A. et al., "Graphene-Based Quantum Capacitance Wireless Vapor Sensors," IEEE Sensors Journal, vol. 14, No. 5, May 2014 (8 pages).

Deen, David A. et al., "Graphene-Based Quantum Capacitance Wireless Vapor Sensors," IEEE Sensors Journal, vol. 14, No. 5, May 2014, pp. 1459-1466 (8 pages).

Droscher, S. et al., "Quantum Capacitance and Density of States of Graphene," Phys. Scr. T146 (2012) 014009, pp. 1-5 (5 pages).

Ebrish, M. A. et al., "Dielectric Thickness Dependence of Quantum Capacitance in Graphene Varactors with Local Metal Back Gates," Device Research Conference, 2012 (2 pages).

Ebrish, M.A. et al., "Operation of multi-finger graphene quantum capacitance varactors using planarized local bottom gate electrodes," Applied Physics Letters, vol. 100, No. 14, Apr. 2012 (4 pages).

"European Search Report," for Dutch Patent Application No. 2019492 dated Apr. 12, 2018 (10 pages).

"European Search Report," for European Patent Application No. 18180455.0 dated Dec. 3, 2018 (5 pages).

"Fdc1004 4-Channel Capacitance-to-Digital Converter for Capacitive Sensing Solutions," Data Sheet SNOSCY5B Texas Instruments Aug. 2014—Revised 2015 (24 pages).

"Fdc1004evm User Guide," Literature Number: SNAU163C, Texas Instruments Aug. 2014—Revised Oct. 2016 (46 pages).

"Final Office Action," for U.S. Appl. No. 14/883,895 dated Sep. 14, 2018 (16 pages)

"First Office Action," for Chinese Patent Application No. 201580056417.2 dated Feb. 11, 2019 (13 pages) with English summary.

Fisher, James P. et al., "Central Sympathetic Overactivity: Maladies and Mechanisms," Autonomic Neuroscience 148.1 (2009): 5-15 (11 pages).

Georgakilas, Vasilios et al., "Functionalization of Graphene: Covalent and Non-Covalent Approaches, Derivatives and Applications," Chemical Reviews, 2012, 14:112(11), pp. 6156-6214.

Hu, Yuhai et al., "Chemically Functionalized Graphene and Their Applications in Electrochemical Energy Conversion and Storage," Advances in Graphene Science, Chapter 7, 2013, pp. 161-190 (30 pages).

"International Preliminary Report on Patentability," for PCT Application No. PCT/US2015/056243 dated May 4, 2017 (8 pages).

"International Preliminary Report on Patentability," for PCT Application No. PCT/US2018/037144 dated Dec. 27, 2018 (7 pages).

"International Search Report and Written Opinion," for PCT Application No. PCT/US2015/056243, dated Jan. 26, 2016 (12 pages).

"International Search Report and Written Opinion," for PCT Application No. PCT/US2017/037144 dated Oct. 6, 2017 (11 pages).

"International Search Report and Written Opinion," for PCT Application No. PCT/US2017/057318 dated Feb. 6, 2018 (14 pages).

"International Search Report and Written Opinion," for PCT Application No. PCT/US2018/033166 dated Oct. 2, 2018 (12 pages).

Koester, Steven J. "Using the Quantum Capacitance in Graphene to Enable Varactors for Passive Wireless Sensing Applications," 2011 IEEE Sensors Proceedings, pp. 994-997, 2011 (4 pages).

Li, Xiao et al., "Digital Health: Tracking Physiomes and Activity Using Wearable Biosensors Reveals Useful Health-Related Information," PLoS Biology 15.1 (2017): e2001402 (30 pages).

Ma, Rui et al., "Acetone Sensing Using Graphene Quantum Capacitance Varactors," 2016 IEEE Sensors, Orlando, FL, 2016 (3 pages).

"Mechanical Data," DGS (S-PDSO-G10) DSC0010B Package Outline, Example Board Layout, and Stencil Design. Texas Instruments 2016 (5 pages).

Nakhleh, Morad K. et al., "Diagnosis and Classification of 17 Diseases from 1404 Subjects via Pattern Analysis of Exhaled Molecules," ACS Nano 2017, 11, 112-125 (14 pages).

"Nano Mobile Healthcare Inc.," Company Profile on Reuters.com URL <http://www.reuters.com/finance/stocks/companyProfile?symbol=VNTH.PK> accessed Mar. 17, 2017 (2 pages).

"Non-Final Office Action," for U.S. Appl. No. 14/883,895 dated Apr. 30, 2018 (37 pages).

"Non-Final Office Action," for U.S. Appl. No. 14/883,895 dated Feb. 15, 2019 (17 pages).

Oprea, A. et al., "Integrated Temperature, Humidity and Gas Sensors on Flexible Substrates for Low-Power Applications," 007 IEEE Sensors, Atlanta, GA, 2007, pp. 158-161 (4 pages).

"Package Materials Information," Tape and Reel Information and Box Dimensions. Texas Instruments Feb. 13, 2016 (2 pages).

"Package Option Addendum," Packaging Information for FDC1004DGSR, DGST, DSCJ, DSCR and DSCT Devices. Texas Instruments May 2015 (2 pages).

"Response to Advisory Action," dated Dec. 3, 2018, for U.S. Appl. No. 14/883,895, submitted via EFS-Web on Dec. 14, 2018, 11 pages.

"Response to Communication Pursuant to Rules 161(1) and 162 EPC," for European Patent Application No. 15790739.5 filed with the EPO Dec. 8, 2017 (14 pages).

"Response to Final Rejection," dated Sep. 14, 2018, for U.S. Appl. No. 14/883,895, submitted via EFS-Web on Nov. 7, 2018, 11 pages.

"Response to Non-Final Office Action," for U.S. Appl. No. 14/883,895, dated Apr. 30, 2018 and filed with the USPTO Jul. 2, 2018 (18 pages).

"Standard Terms and Conditions for Evaluation Modules," Texas Instruments 2016 (5 pages).

Tripathi, Kumud M. et al., "Recent Advances in Engineered Graphene and Composites for Detection of Volatile Organic Compounds (VOCs) and Non-Invasive Diseases Diagnosis," Carbon 110 (2016)97-129 (34 pages).

Wang, David "FDC1004: Basics of Capacitive Sensing and Applications," Application Report SNOA927, Texas Instruments Dec. 2014 (12 pages).

International Search Report and Written Opinion for PCT Application No. PCT/US2019/081744 dated Jun. 28, 2019 (16 pages).

Invitation to Pay Additional Fees and, Where Applicable, Protest Fee for PCT Application No. PCT/US2019/018744 dated May 7, 2019 (11 pages).

"International Preliminary Report on Patentability," for PCT Application No. PCT/US2019/056766 dated Apr. 29, 2021 (10 pages).

"Response to Communication pursuant to Rules 161(1) and 162 EPC," for European Patent Application No. 19711730.2 filed Apr. 12, 2021 (9 pages).

"Communication Pursuant to Article 94(3) EPC," for European Patent Application No. 19711730.2 dated Aug. 27, 2021 (4 pages).

* cited by examiner

BREATH SAMPLING MASK AND SYSTEM

This application claims the benefit of U.S. Provisional Application No. 62/632,552, filed Feb. 20, 2018, the content of which is herein incorporated by reference in its entirety.

FIELD OF THE TECHNOLOGY

The present application relates to a breath sampling mask and systems and methods related to the same.

BACKGROUND

The accurate detection of diseases can allow clinicians to provide appropriate therapeutic interventions. The early detection of diseases can lead to better treatment outcomes. Diseases can be detected using many different techniques including analyzing tissue samples, analyzing various bodily fluids, diagnostic scans, genetic sequencing, and the like.

Some disease states result in the production of specific chemical compounds. In some cases, volatile organic compounds (VOCs) released into a gaseous sample of a patient can be hallmarks of certain diseases. The detection of these compounds or differential sensing of the same can allow for the early detection of particular disease states.

The breath of a patient provides an ideal gas for diagnostic sampling purposes. As a part of tidal respiration, air is drawn in through the nose and/or mouth and into the lungs. By its presence in close contact with moist internal tissues, the inspired air is warmed, humidified, and picks up volatile organic compounds. This air is then expired out through the nose and/or mouth.

SUMMARY

In a first aspect, a breath sensing system is included. The breath sampling system can include a breath sampling mask. The breath sampling mask can include a mask housing configured to cover a portion of the face of a patient, the mask housing defining a breath receiving chamber. The breath sampling system can also include a chemical sensor element in fluid communication with the breath sampling mask. The chemical sensor element can include a plurality of discrete binding detectors. The chemical sensor element can be configured to interface with a breath sample collected through the breath sampling mask.

In a second aspect, in addition to one or more of the preceding or following aspects, or in the alternative to some aspects, the breath sensing system can include circuitry for generating signals from the discrete binding detectors.

In a third aspect, in addition to one or more of the preceding or following aspects, or in the alternative to some aspects, the breath sensing system can include a breath sampling mask including a nose clip for helping to secure the breath sampling mask to the face of a patient.

In a fourth aspect, in addition to one or more of the preceding or following aspects, or in the alternative to some aspects, the breath sensing system can include a sensor such as one or more of a temperature sensor, a heart rate sensor, and a blood pressure sensor.

In a fifth aspect, in addition to one or more of the preceding or following aspects, or in the alternative to some aspects, the breath sensing system can include a sensor such as one or more of an ambient temperature sensor, an ambient humidity sensor, an internal temperature sensor, and an internal humidity sensor.

In a sixth aspect, in addition to one or more of the preceding or following aspects, or in the alternative to some aspects, the breath sensing system can include a removable breath sample container disposed within the mouth chamber.

In a seventh aspect, in addition to one or more of the preceding or following aspects, or in the alternative to some aspects, the breath sensing system can include a gas outflow conduit in fluid communication with the breath receiving chamber.

In an eighth aspect, in addition to one or more of the preceding or following aspects, or in the alternative to some aspects, the breath sensing system can include a chemical sensor holder configured to allow removable mounting of a chemical sensor element.

In a ninth aspect, in addition to one or more of the preceding or following aspects, or in the alternative to some aspects, the chemical sensor holder can be disposed within the breath receiving chamber.

In a tenth aspect, in addition to one or more of the preceding or following aspects, or in the alternative to some aspects, the breath sensing system can include a chemical sensor holder housing in fluid communication with the breath receiving chamber, wherein the chemical sensor element can be disposed within the chemical sensor holder housing.

In an eleventh aspect, in addition to one or more of the preceding or following aspects, or in the alternative to some aspects, the breath sensing system can include a filter in fluid communication with the one-way airflow valve.

In a twelfth aspect, in addition to one or more of the preceding or following aspects, or in the alternative to some aspects, a breath sampling mask is included. The breath sampling mask can include a mask housing configured to cover a portion of the face of a patient. The mask housing can define a chamber. The mask configured to remove volatile organic compounds from air drawn in through the mask housing.

In a thirteenth aspect, in addition to one or more of the preceding or following aspects, or in the alternative to some aspects, the breath sampling mask can include a sensor such as one or more of a temperature sensor, a heart rate sensor, and a blood pressure sensor.

In a fourteenth aspect, in addition to one or more of the preceding or following aspects, or in the alternative to some aspects, the breath sampling mask can include a nose clip member for helping to secure the breath sampling mask to the patient.

In a fifteenth aspect, in addition to one or more of the preceding or following aspects, or in the alternative to some aspects, a sensor can be attached to a nose clip member.

In a sixteenth aspect, in addition to one or more of the preceding or following aspects, or in the alternative to some aspects, the mask housing of the breath sampling mask can include a dividing wall isolating the chamber into a nasal chamber and a mouth chamber.

In a seventeenth aspect, in addition to one or more of the preceding or following aspects, or in the alternative to some aspects, the breath sampling mask can include a one-way airflow valve in fluid communication with the nasal chamber and an area outside of the mask housing, where the one-way airflow valve only allows a flow of air from the area outside of the mask housing into the nasal chamber.

In an eighteenth aspect, in addition to one or more of the preceding or following aspects, or in the alternative to some aspects, the breath sampling mask can include a chemical sensor holder configured to allow removable mounting of a chemical sensor element. The chemical sensor holder can be disposed within the mouth chamber of the breath sampling mask.

In a nineteenth aspect, in addition to one or more of the preceding or following aspects, or in the alternative to some aspects, the breath sampling mask can include a sensor such as one or more of an ambient temperature sensor, an ambient humidity sensor, an internal temperature sensor, and an internal humidity sensor.

In a twentieth aspect, in addition to one or more of the preceding or following aspects, or in the alternative to some aspects, a method of determining the presence of one or more disease states of a patient is included. The method can include putting a breath sampling mask on a patient; alerting the patient to breathe in and out to generate a breath sample; contacting the breath sample with a chemical sensor element, the chemical sensor element including a plurality of discrete binding detectors; using a measurement circuit to generate signals from the discrete binding detectors; and evaluating the signals by comparing them to previously obtained sets of signals or signal patterns.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope of the present application is defined by the appended claims and their legal equivalents.

BRIEF DESCRIPTION OF THE FIGURES

The technology may be more completely understood in connection with the following drawings, in which.

While the technology is susceptible to various modifications and alternative forms, specifics thereof have been shown by way of example and drawings, and will be described in detail. It should be understood, however, that the application is not limited to the particular embodiments described. On the contrary, the application is to cover modifications, equivalents, and alternatives falling within the spirit and scope of the technology.

DETAILED DESCRIPTION

The breath of a patient provides an ideal gas for diagnostic sampling purposes. As a part of tidal respiration, air is drawn in through the nose and/or mouth and into the lungs. By its presence in close contact with moist internal tissues, the inspired air is warmed, humidified, and picks up volatile organic compounds (VOCs). This air is then expired out through the nose and/or mouth.

In some instances, the VOCs present in exhaled breath can be hallmarks of certain diseases, including but not limited to cancers, including lung cancer, blood-borne cancers, prostate cancer, rectal cancer, breast cancer, liver cancer, pancreatic cancer, or to other disorders such as chronic obstructive pulmonary disease, diabetes, heart failure, and the like. Detection of VOCs in the breath of a patient directly from the gaseous form can provide an accurate mechanism for determining one or more diseased states.

Figure 1:
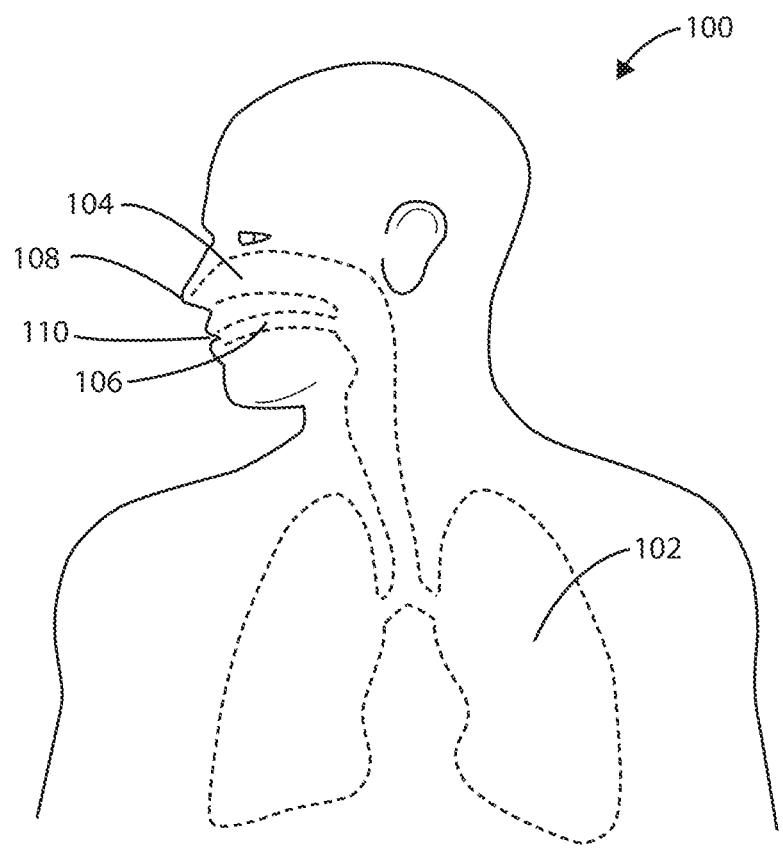
FIG. 1 is a schematic view of a patient showing portions of respiratory pathways.

Referring now to FIG. 1, a schematic view is shown of a patient 100 showing portions of respiratory pathways. Air can be inspired through the nose 108 and into nasal passages 104 or through the mouth 110 and into oral passages 106 eventually reaching the lungs 102. The inspired air is warmed, humidified, and picks up volatile organic compounds during its passage to the lungs, while it remains in the lungs, and further during expiration on its way back out of the lungs. The air is then expired through the nasal passages 104 and out the nose 108 and/or through oral passages 106 and out the mouth 110.

Figure 2:
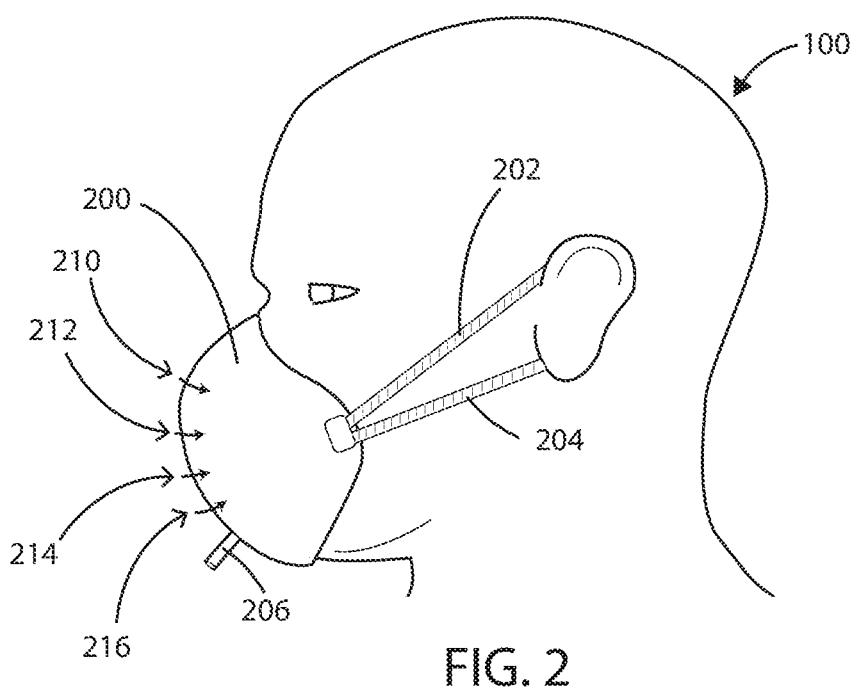
FIG. 2 is a schematic view of a breath sampling mask as worn by a patient in accordance with various embodiments herein.

In accordance with various embodiments herein, a breath sampling mask is included which can aid in one or more of: capturing breath samples, controlling how the breath samples are generated and treated, and providing additional data regarding the patient and/or their current physiological state. FIG. 2 is a schematic view of a breath sampling mask 200 as worn by a patient 100 in accordance with various embodiments herein. The breath sampling mask 200 can include one or more elastic members 202, 204 configured to secure the breath sampling mask 200 to the patient's face. The pressure of the breath sampling mask 200 on the face can aid in forming an air tight connection of the breath sampling mask 200 to the patient's face.

In the embodiment of FIG. 2, when the patient creates a negative pressure inside the breath sampling mask 200, air can be drawn from the ambient environment into the breath sampling mask 200 through the exterior surface of breath sampling mask 200 (or a portion thereof), as indicated in FIG. 2 by air inflow arrows 210, 212, 214, and 216. As such, the breath sampling mask 200, or portions thereof, can be made of a porous material (one or more layers of material) to allow air to be drawn in, in this way. Porous materials can include, but are not limited to, woven and non-woven fibrous materials, porous cellulosic materials, porous polymers, porous or non-porous materials assuming porous structures such as grids, weaves, sieves, and the like. However, in other embodiments, the breath sampling mask 200, or portions thereof, can be made of a non-porous material. Non-porous materials can include, but are not limited to, polymers, metals, cellulosic materials, composites, metals, ceramics, and the like.

In some embodiments, breath sampling mask 200 can include filters or conditioned surfaces to treat the incoming air such that it can do one or more of: filtering particulate matter from the air, providing humidity control, providing a filter for organic or inorganic matter, and providing for adsorption of compounds and/or particulates in the ambient environment. By way of example, a carbon surface can be included on the exterior to filter out environmental particulates and/or environmental volatile organic compounds (VOCs). For example, a carbon material can be sprayed on, or otherwise applied to, an outer surface of the breath sampling mask 200. In some embodiments, the breath sampling mask 200 can include a carbon layer disposed within the mask itself. For example, a carbon material can be integrated into a material layer used to make the breath sampling mask 200 and/or sandwiched in between layers of material used to make the breath sampling mask 200. Carbon herein can be specifically be carbon that can absorb significant amounts of VOCs through high surface area such as activated carbon or activated charcoal (in some cases one gram of activated carbon has a surface area in excess of 3,000 m$^2$ or more) and/or through the use of chemical treatments to enhance absorption properties.

The breath sampling mask 200 can include various ports or conduits in and out of the breath sampling mask 200, some of which may be in fluid communication with valves or other components or portions of the breath sampling mask 200. By way of example, the breath sampling mask 200 can include one or more conduits 206, which can serve as a passageway for breath samples, exhaust air, wires, or the like.

Figure 3:
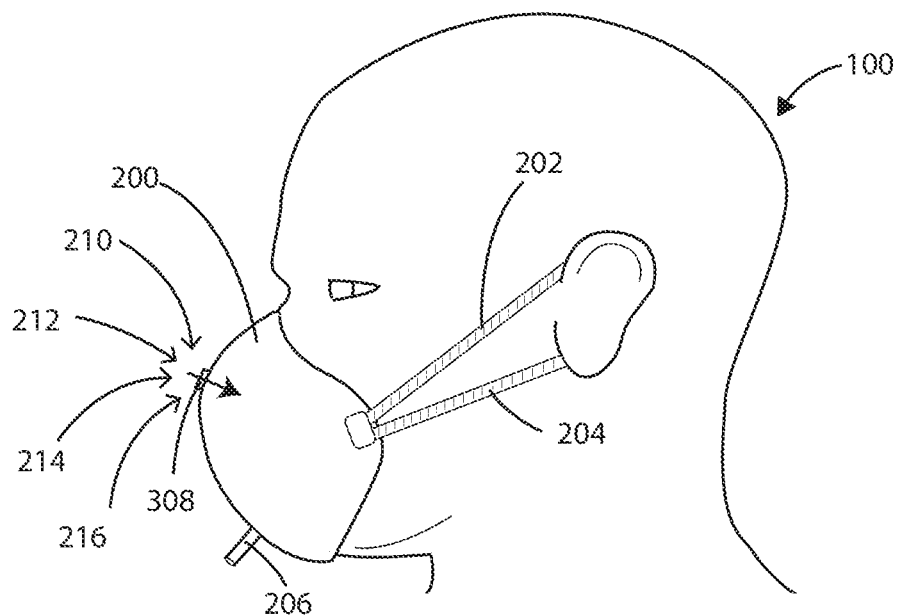
FIG. 3 is a schematic view of a breath sampling mask as worn by a patient in accordance with various embodiments herein.

In the embodiment of FIG. 2, air is primarily drawn in through the mask housing material itself, however, in other embodiments an incoming port or conduit can be used through which air is drawn in. FIG. 3 is a schematic view of a breath sampling mask 200 as worn by a patient 100 in accordance with various embodiments herein. The breath sampling mask 200 can include one or more elastic members 202, 204 configured to secure the breath sampling mask 200 to the patient's face. The breath sampling mask 200 can include various ports or conduits in and out of the breath sampling mask 200, some of which may be in fluid communication with valves or other components or portions of the breath sampling mask 200. By way of example, in some embodiments, the breath sampling mask 200 can include an air intake port 308. When the patient creates a negative pressure inside the breath sampling mask 200, air can be drawn from the ambient environment into the breath sampling mask 200 through the air intake port 308, as indicated in FIG. 3 by air inflow arrows 210, 212, 214, and 216. The breath sampling mask 200 can also include one or more conduits 206, which can serve as a passageway for breath samples, exhaust air, wires, or the like.

It may be desirable to pre-condition and/or filter the inhaled air prior to its passage through the mask housing or port 308. In some embodiments, a preconditioning unit (not shown) can be connected to an air intake port 308 via a suitable connector, such as a bayonet connector. Pre-conditioning and/or filtering the inhaled air can include, but not be limited to, providing humidity control, providing temperature control, filtering particulate matter from the air, filtering organic or inorganic matter, including VOCs, by providing for adsorption and/or absorption of compounds and/or particulates from the ambient environment.

Figure 4:
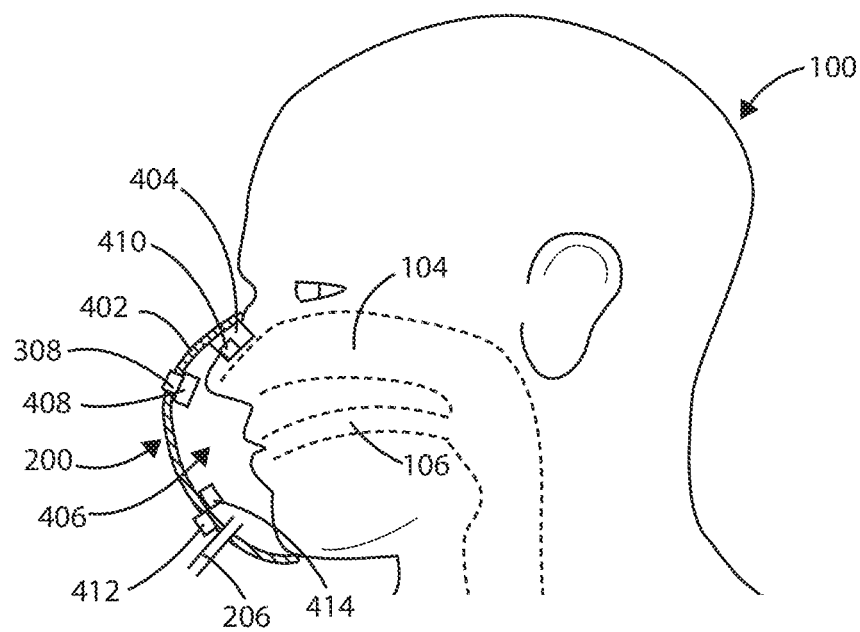
FIG. 4 is a schematic cutaway view of a breath sampling mask as worn by a patient in accordance with various embodiments herein.

Referring now to FIG. 4, a schematic cutaway view of a breath sampling mask 200 as worn by a patient 100 is shown in accordance with various embodiments herein. The breath sampling mask 200 includes a mask housing 402 that is configured to cover a portion of the face of the patient 100. The mask housing 402 can define an interior chamber 406, which can be a breath receiving chamber. The breath sampling mask 200 can also include a nose clip member 404 connected to the mask housing 402 for helping to secure the breath sampling mask 200 to the patient 100. In some embodiments, the nose clip member 404 can work in collaboration with the elastic members 202, 204, to form an air tight connection of the breath sampling mask 200 against the patient's face. In some embodiments, breath sampling mask 200 can include a gas outflow conduit 206 in fluid communication with the breath receiving chamber.

The nose clip member 404 can take on various forms and be make of various materials. In some embodiments, the nose clip member 404 can include a U-shaped or V-shaped member which can exert at least some pressure on a patient's nose from two-directions that are at least partially opposed. In some embodiments, the nose clip member 404 can include a spring-like element which can expand under applied force to allow the nose clip member to fit over a patient's nose, but then exert pressure on the nose when the applied force is released. Materials used to form the nose clip member 404 can include, but are not limited to, polymers, metals, composites, and the like.

In various embodiments, the breath sampling mask 200 can include a one-way airflow valve 408. The one-way airflow valve 408 can be in fluid communication between the air intake port 308 and the interior chamber 406, the one-way airflow valve 408 only allowing a flow of air from the area outside of the mask housing 402 into the interior chamber 406. In some embodiments, a filter can be placed in fluid communication with one-way airflow valve 408 such that it can remove particulate or chemical impurities from the environmental air prior to being inhaled by patient 100. In some embodiments, the filter can be integrated with the valve 408 structure. The filter can do one or more of filter out particulate matter from inspired air, provide humidity control, provide a filter for organic or inorganic matter, and/or provide for adsorption of compounds and/or particulates in the ambient environment. By way of example, the filter can include a carbon material, such as those described above, to filter out environmental particulates and/or environmental volatile organic compounds (VOCs).

In some embodiments, the breath sampling mask 200 can include a sensor 410 that can be connected to the nose clip member 404. In some embodiments, the sensor 410 can be configured to contact the skin of the patient 100 when the mask housing 402 is worn by the patient 100. The sensor 410 can be selected from a group including a temperature sensor, a heart rate sensor, and a blood pressure sensor.

It will be appreciated that while the sensor 410 in FIG. 4 is shown as being connected to the nose clip member 404 and in contact with the skin of the patient, other embodiments for the sensor 410 can be contemplated. For example, in some embodiments the sensor 410 can include an ear clip sensor, a fingertip sensor, a carotid artery sensor, or a galvanic skin sensor that is not integral with the mask, but connected to the mask housing via a wired or wireless connection. In some embodiments the sensor 410 can include non-contact sensors (e.g., that does not contact the skin), such as those used in electromagnetic-based, laser-based, and image-based sensor systems.

In some embodiments, the breath sampling mask 200 can also include additional sensors 412, 414, which can be on the outside of the breath sampling mask 200 or on the inside of the breath sampling mask 200. Exemplary sensors can include an ambient temperature sensor, an ambient humidity sensor, an internal temperature sensor, and an internal humidity sensor.

Figure 5:
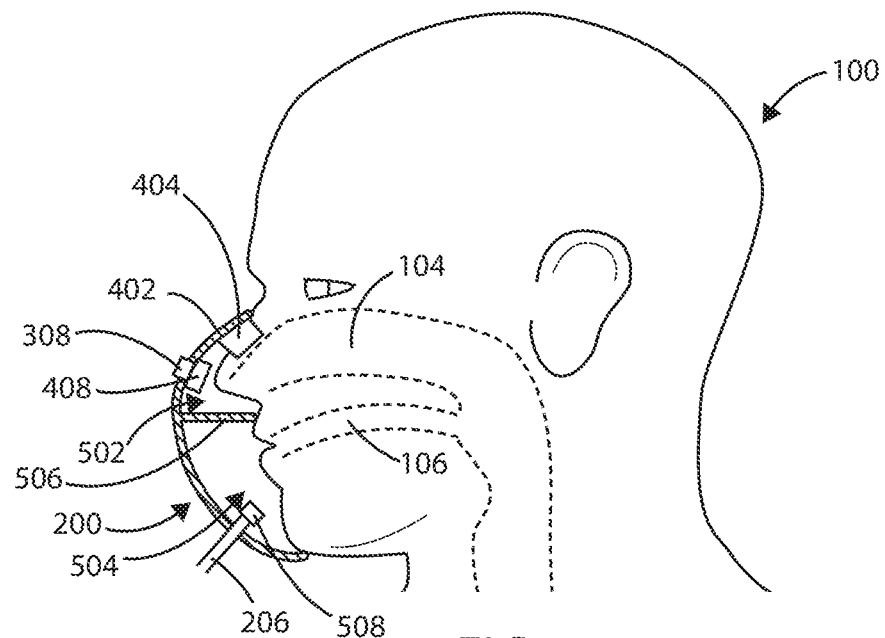
FIG. 5 is a schematic cutaway view of a breath sampling mask as worn by a patient in accordance with various embodiments herein.

While the embodiment of FIG. 4 shows a single chamber inside the mask, it will be appreciated that other embodiments of masks herein can include multiple chambers that are isolated from one another. The mask can be configured to allow air and breath samples to move through the chambers of the mask in only a particular way or direction. FIG. 5 is a schematic cutaway view of a breath sampling mask 200 as worn by a patient in accordance with various embodiments herein. In this embodiment, the breath receiving chamber includes dividing wall 506 to isolate breath receiving chamber into a nasal chamber 502 and a mouth chamber 504, as defined by the mask housing 402. The nasal chamber 502 and the mouth chamber 504 can be separated from one another when the breath sampling mask 200 comes into contact with the face of patient during usage.

Separating the interior volume defined by the mask housing 402 into nasal chambers 502 and mouth chambers 504, in combination with valves, can allow for a controlled unidirectional flow of air through the breath sampling mask 200. In particular, the one-way airflow valve 408 only allows a flow of air from the area outside of the mask housing 402 into the nasal chamber 502 through air intake port 308. Further another one-way airflow valve 508 only allows a flow of air from the mouth chamber 504 out through conduit 206. In this manner, air only moves through the chambers of the breath sampling mask 200 in one direction. It will be appreciated that while air intake port 308 and one-way airflow valve 408 are shown disposed in the mask housing 402 within the nasal chamber 502, the air intake port 308 and one-way airflow valve 408 can alternatively be disposed in the mask housing 402 within the mouth chamber 504. In some embodiments, the air intake port 308 and one-way airflow valve 408 can be disposed in the mask housing 402 in both the nasal chamber 502 and within the mouth chamber 504. In some embodiments, breath sampling mask 200 can include a gas outflow conduit 206 in fluid communication with the nasal chamber 502, the mouth chamber 504, or both.

Figure 6:
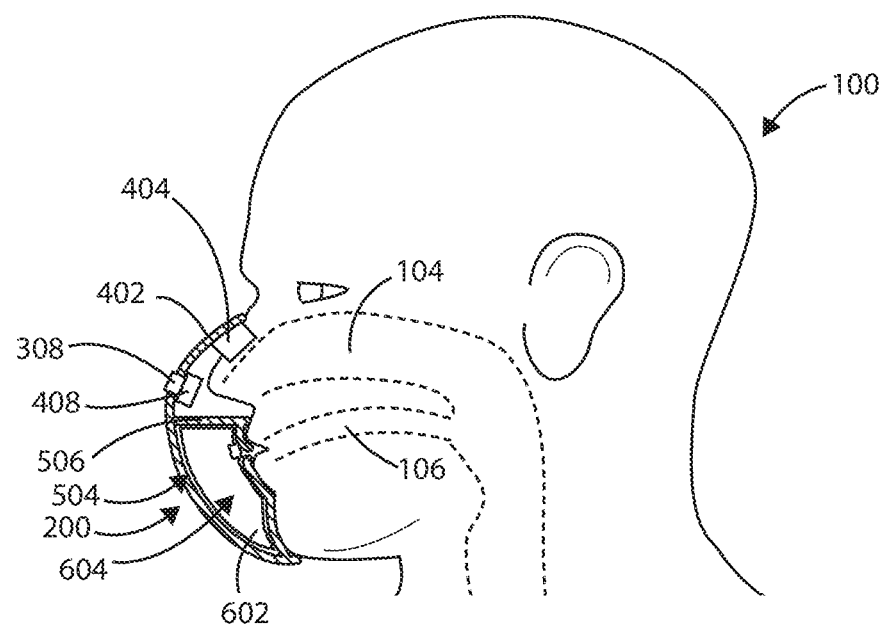
FIG. 6 is a schematic cutaway view of a breath sampling mask as worn by a patient in accordance with various embodiments herein.

In some embodiments, it may be desirable to retain a breath sample within the breath sampling mask 200 itself or another associated structure. For example, a container can be used to hold a breath sample, and the container itself can be disposed in the breath sampling mask 200 or otherwise in fluid communication with the breath sampling mask 200. Referring now to FIG. 6, a schematic cutaway view of a breath sampling mask 200 as worn by a patient 100 is shown in accordance with various embodiments herein. In this view, a breath sample container 602 is disposed within the mouth chamber 504. The breath sample container 602 can define an interior volume 604 in order to hold and retain a breath sample. It will be appreciated that while the breath sample container 602 shown in FIG. 6 is removable, in another embodiment, breath sample container 602 could be an integral part of the breath sampling mask 200.

Figure 7:
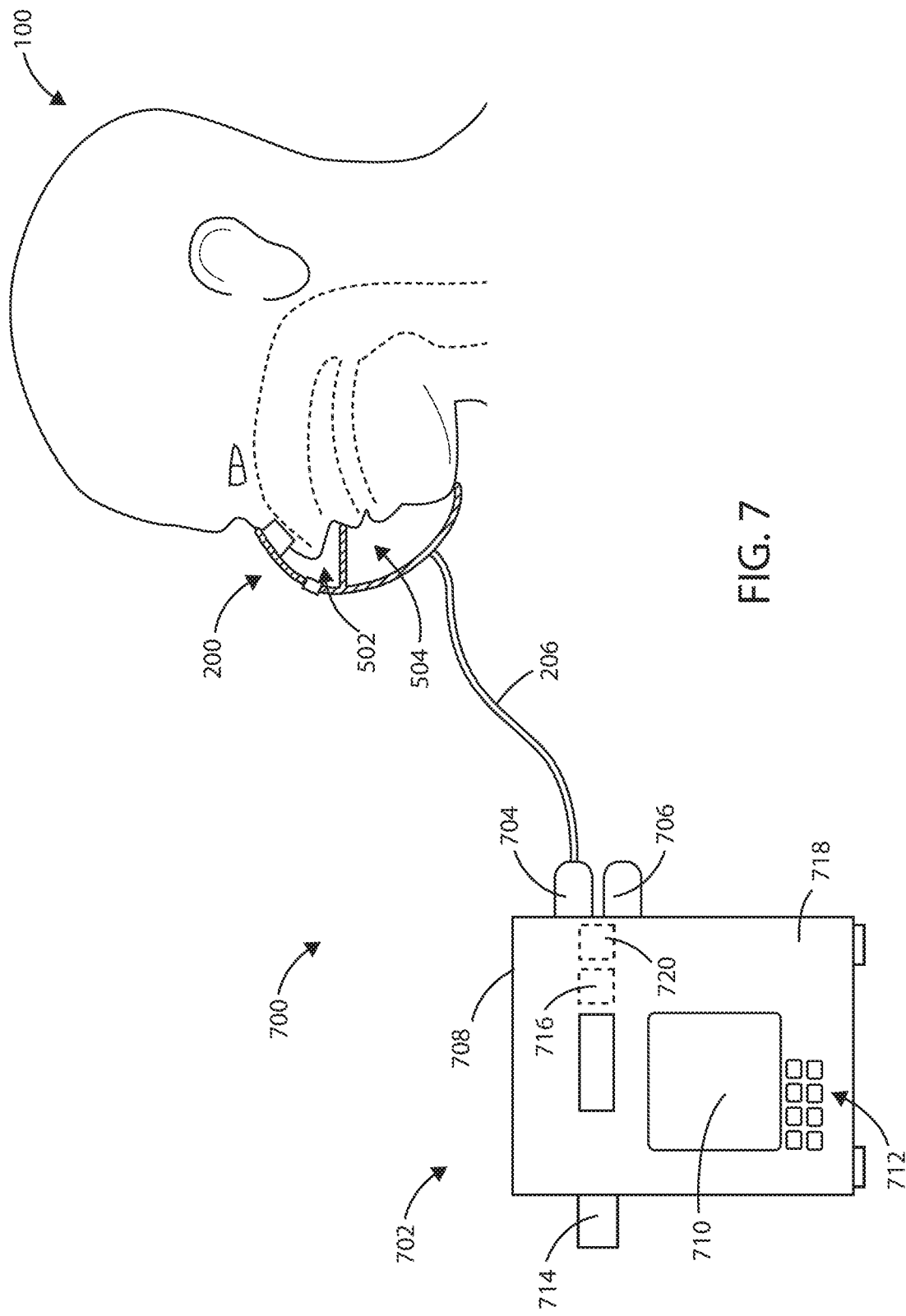
FIG. 7 is a schematic view of a breath sampling system in accordance with various embodiments herein.

Breath sampling masks in accordance with embodiments herein can form parts of breath sampling systems. Such breath sampling systems can include a breath sampling mask along with other components such as chemical sensors including sensing elements and circuitry for generating signals based on electrical properties of the sensing elements. Referring now to FIG. 7, a schematic view is shown of a breath sampling system 700 in accordance with various embodiments herein. The breath sampling system 700 can include breath sampling mask 200, which can be worn by a patient 100. In the embodiment shown in FIG. 7, air can be inspired into a nasal chamber 502 and into the lungs of the patient 100. This air can then be expired out into a mouth chamber 504 before passing out through conduit 206 and on to a gaseous analyte sensing device 702 for analysis.

The gaseous analyte sensing device 702 can include a housing 718. The gaseous analyte sensing device 702 can be connected to breath sampling mask 200 via conduit 206, through which a patient's gaseous breath sample can travel to be evaluated at gaseous analyte sensing device 702. The patient's gaseous breath sample can pass through an evaluation sample (patient sample) input port 704. The gaseous analyte sensing device 702 can also include a control sample (environment) input port 706. The gaseous analyte sensing device 702 can also include a chemical sensor element chamber 708, into which a chemical sensor element can be placed. The gaseous analyte sensing device 702 can also include a display screen 710 and a user input device 712, such as a keyboard. The gaseous analyte sensing device 702 can also include a gas outflow port 714. The gaseous analyte sensing device 702 can also include flow sensors in fluid communication with the gas flow associated with one or more of the evaluation sample input port 704 and control sample input port 706. It will be appreciated that many different types of flow sensors can be used. In some embodiments, a hot-wire anemometer can be used to measure the flow of air. In some embodiments, the gaseous analyte sensing device 702 can include a $CO_2$ sensor in fluid communication with the gas flow associated with one or more of the evaluation sample input port 704 and control sample input port 706.

In various embodiments, the gaseous analyte sensing device 702 can also include other functional components. By way of example, the gaseous analyte sensing device 702 can include a humidity control module 716 and/or a temperature control module 720. The humidity control module 716 can be in fluid communication with the gas flow associated with one or more of the evaluation sample input port 704 and control sample input port 706 in order to adjust the humidity of one or both gas flow streams in order to make the relative humidity of the two streams substantially the same in order to prevent an adverse impact on the readings obtained by the system. The temperature control module 720 can be in fluid communication with the gas flow associated with one or more of the evaluation sample input port 704 and control sample input port 706 in order to adjust the temperature of one or both gas flow streams in order to make the temperature of the two streams substantially the same in order to prevent an adverse impact on the readings obtained by the system. By way of example, the air flowing into the control sample input port can be brought up to 37 degrees Celsius in order to match the temperature of air coming from a patient. The humidity control module and the temperature control module can be upstream from the input ports, within the input ports, or downstream from the input ports in the housing 718 of the gaseous analyte sensing device 702. In some embodiments, the humidity control module 716 and the temperature control module 720 can be integrated.

Figure 8:
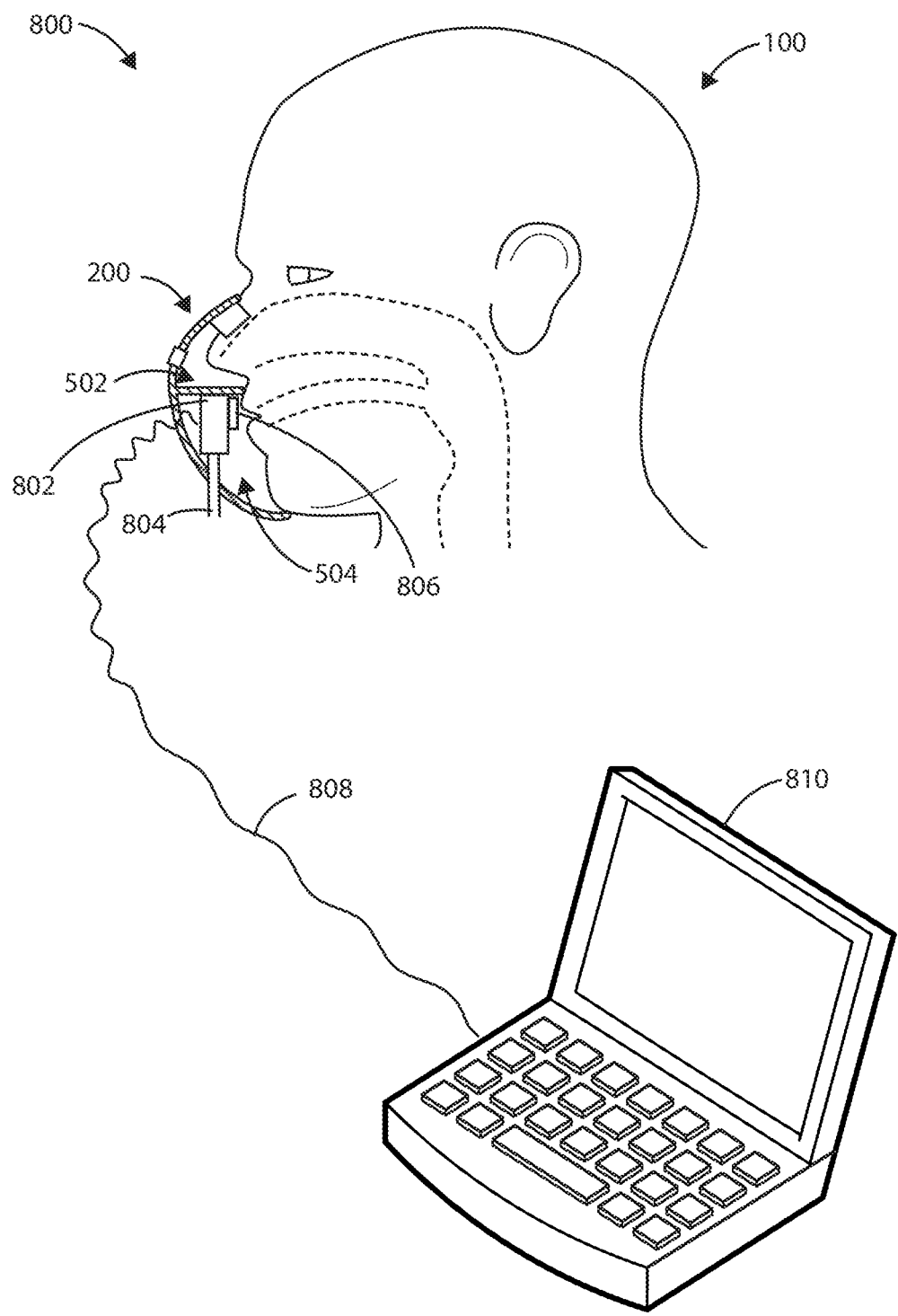
FIG. 8 is a schematic view of a breath sampling system in accordance with various embodiments herein.

In some embodiments, breath samples can be put into contact with a chemical sensor element in the mask itself or in a structure directly attached to the mask. One or more components of the gaseous analyte sensing device 702 shown in reference to FIG. 7 can be integrated into the breath sampling mask 200. As such, in some embodiments, a separate gaseous analyte sensing device may not be needed in a breath sensing system. Referring now to FIG. 8, a schematic view is shown of a breath sampling system 800 in accordance with various embodiments herein. The breath sampling system 800 can include a breath sampling mask 200 including a nasal chamber 502 and a mouth chamber 504. A chemical sensor holder 802 can be disposed within a breath receiving chamber, such as mouth chamber 504. The chemical sensor holder 802 can be configured to allow removable mounting of a chemical sensor element. The chemical sensor element can interface with a breath sample collected through the breath sampling mask 200 when the patient 100 exhales into the breath sampling mask 200. Exemplary chemical sensor elements will be described more fully below in reference to FIGS. 18-21.

Figure 9:
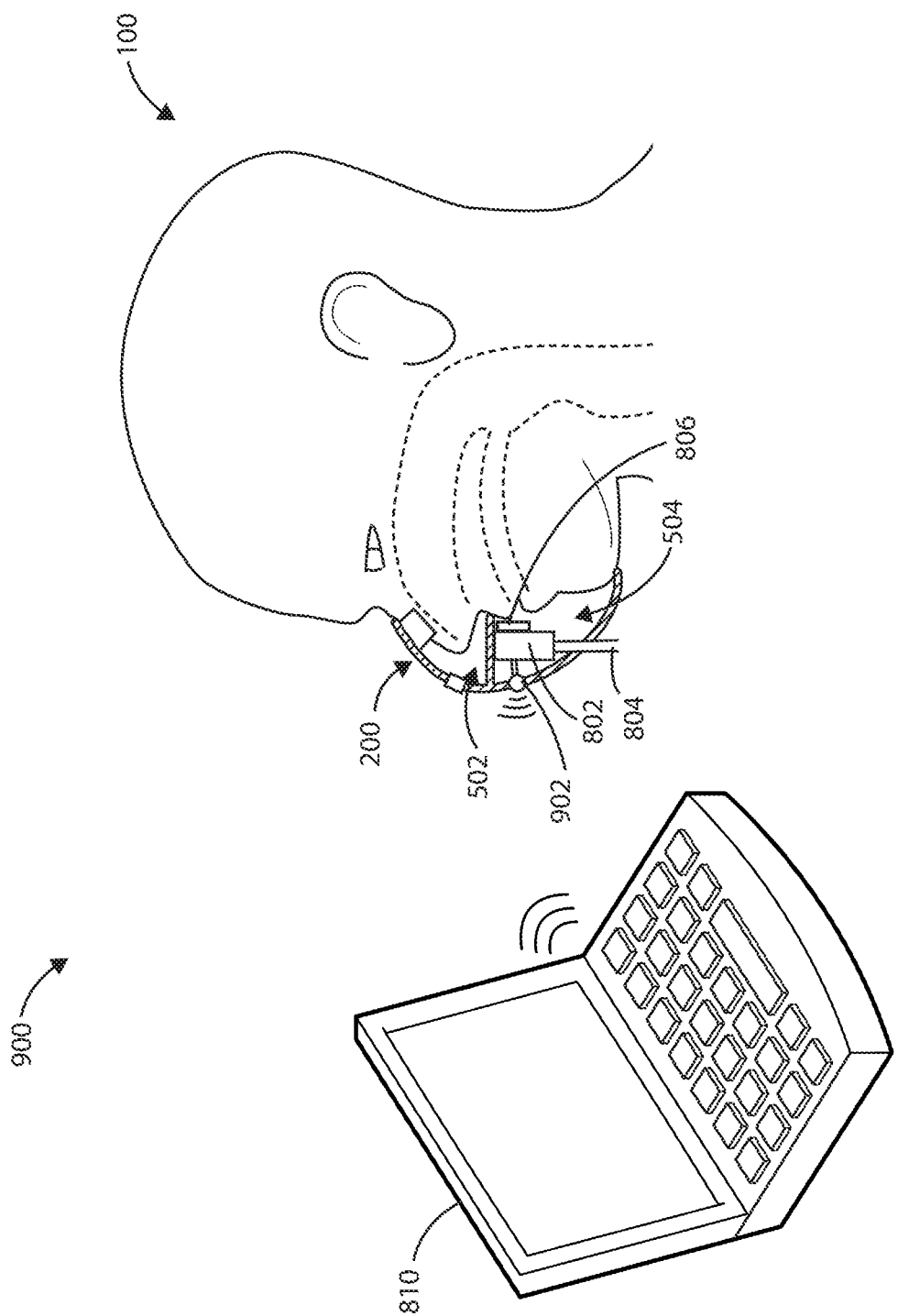
FIG. 9 is a schematic view of a breath sampling system in accordance with various embodiments herein.

Sample gas (breath) can optionally pass through a structure 806 such as a filter or valve and into the chemical sensor holder 802. After entering the chemical sensor holder 802, the gas can then pass out of the system through an exhaust port 804. Measurement circuitry (not shown in this view) can be associated with the chemical sensor holder 802 in order to generate a signal based on an electrical property of the chemical sensor element. The signal(s) can be conveyed to an analysis device 810 through a data conduit 808. It will be appreciated, however, that signals can also be conveyed wirelessly. Referring now to FIG. 9, a schematic view is shown of a breath sampling system 900 in accordance with various embodiments herein. In this embodiment, the breath sampling system 900 includes communication circuitry and an antenna 902 in order to generate wireless signals that can be received by an analysis device 810.

Figure 10:
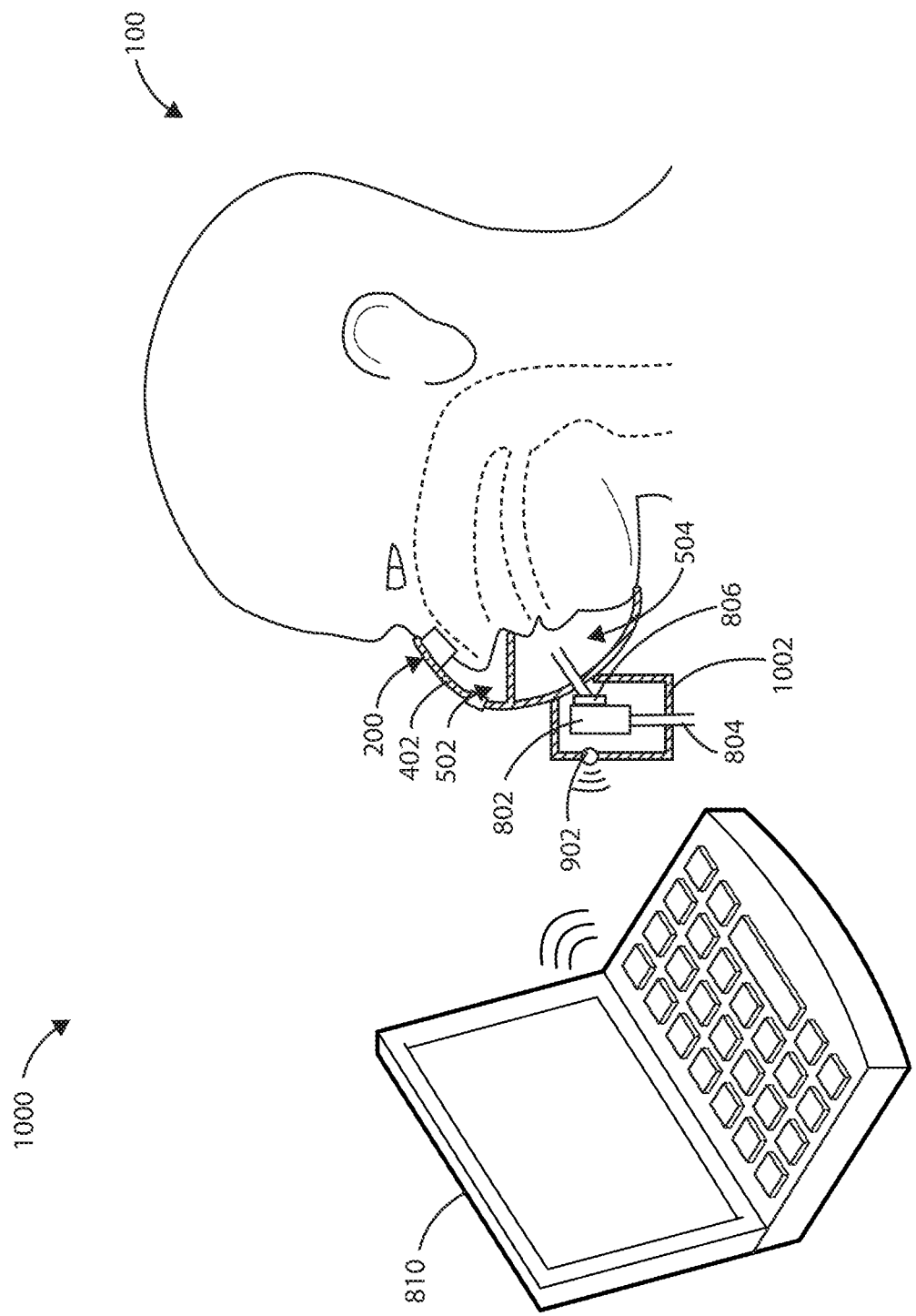
FIG. 10 is a schematic view of a breath sampling system in accordance with various embodiments herein.

In some embodiments, the chemical sensor holder 802 can be housed in a separate structure that can be attached (removably or not) to the breath sampling mask 200. Referring now to FIG. 10, a schematic view is shown of a breath sampling system 1000 in accordance with various embodiments herein. In this embodiment, a chemical sensor holder housing 1002 is included. The chemical sensor holder housing can be in fluid communication with the breath receiving chamber. Sample gas can pass from the mouth chamber 504 into chemical sensor holder housing 1002 and, specifically, into the chemical sensor holder 802 located within the chemical sensor holder housing 1002. Sample gas can pass over chemical sensor element (not shown), secured by chemical sensor holder 802, and out exhaust port 804.

Figure 11:
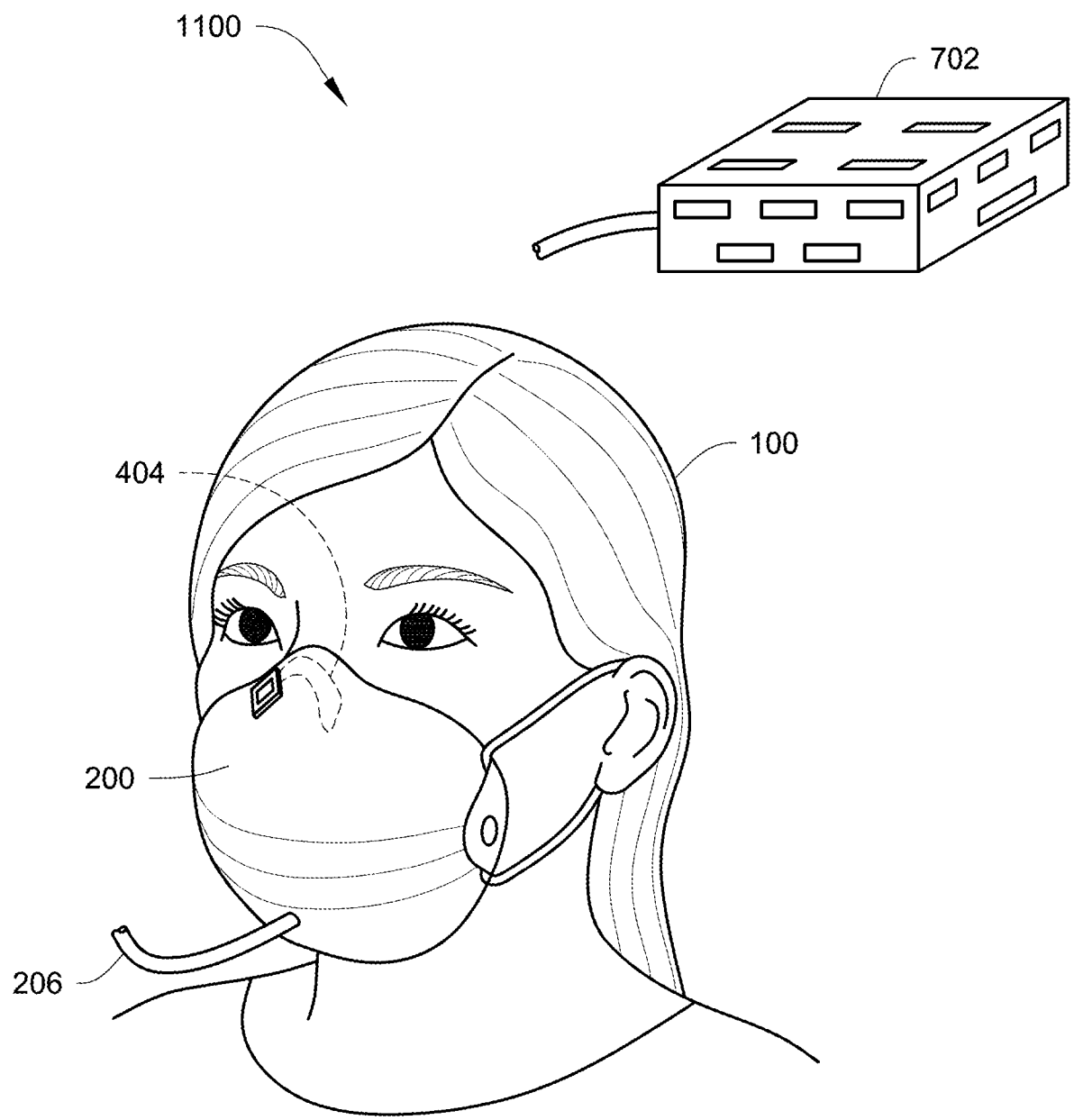
FIG. 11 is a schematic view of a breath sampling system in accordance with various embodiments herein.

It will be appreciated that mask herein can take on many different specific forms. Referring now to FIG. 11, a schematic view is shown of a breath sampling system 1100 in accordance with various embodiments herein. The breath sampling system 1100 can include breath sampling mask 200, which can be worn by a patient 100. Breath sampling mask 200 can include nose clip member 404 for helping to secure the breath sampling mask 200 to the patient 100. In the embodiment shown in FIG. 11, air can be inspired into the mask and into the lungs of the patient 100. This air can then be expired out into a mouth chamber before passing out through conduit 206 and on to a gaseous analyte sensing device 702. In some embodiments, the breath sampling mask 200 and gaseous analyte sensing device 702 can be connected directly via a data conduit, such as data conduit 808 shown in FIG. 8. In other embodiments, the breath sampling mask 200 and gaseous analyte sensing device 702 can be connected wirelessly.

Figure 12:
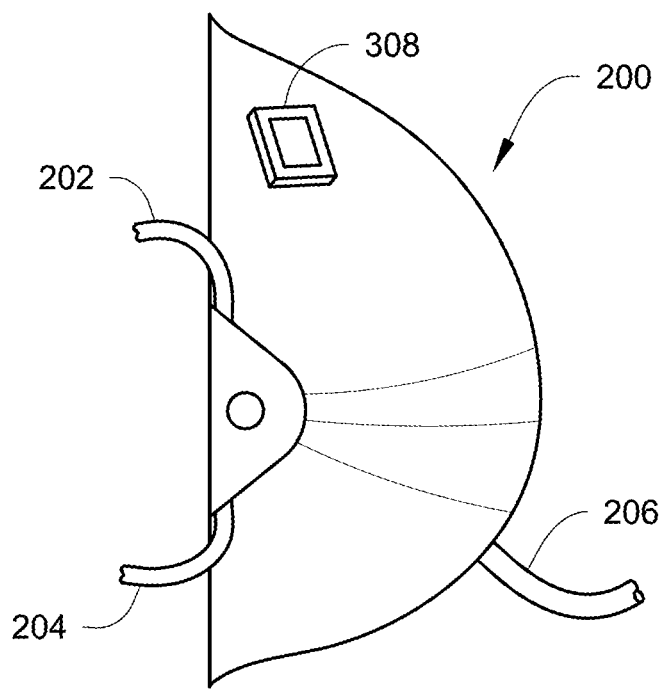
FIG. 12 is a schematic view of a breath sampling mask in accordance with various embodiments herein.
Figure 13:
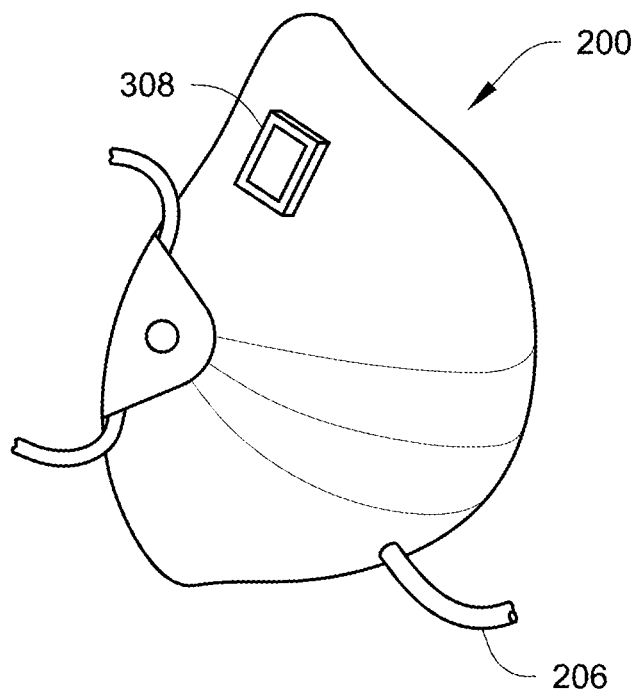
FIG. 13 is a schematic view of a breath sampling mask in accordance with various embodiments herein.
Figure 14:
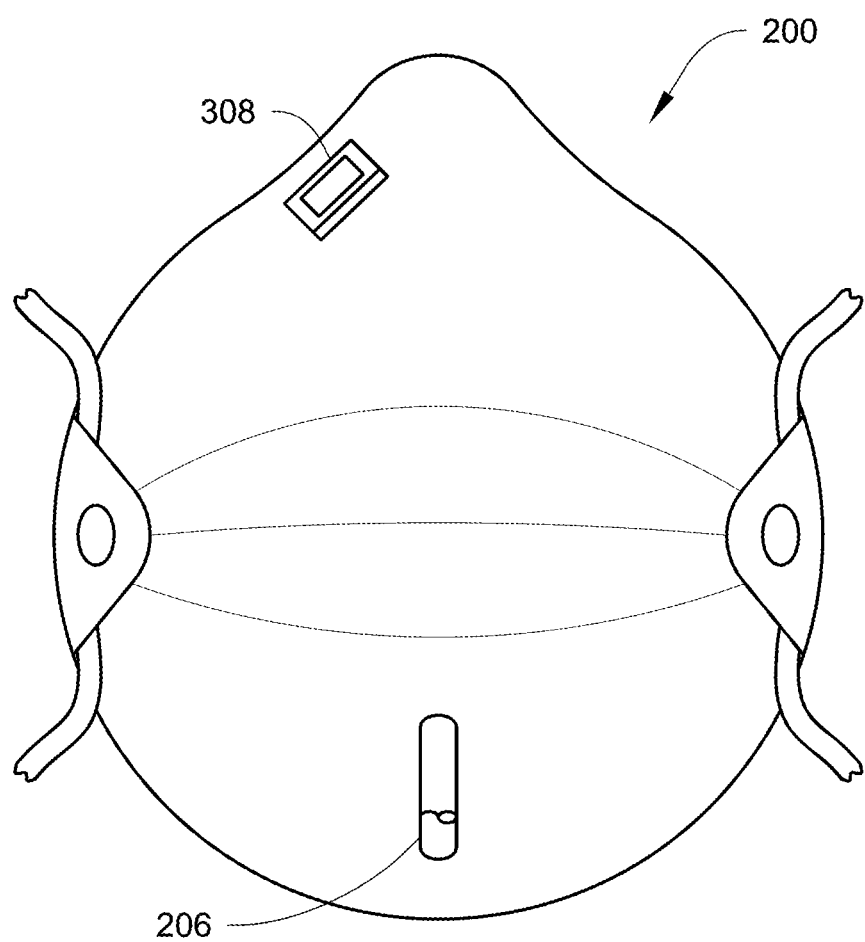
FIG. 14 is a schematic view of a breath sampling mask in accordance with various embodiments herein.

The embodiment of breath sampling mask 200 shown in FIG. 11 will be described in more detail in reference to FIGS. 12-17. Referring now to FIG. 12, a schematic side view of an exterior of breath sampling mask 200 is shown. Breath sampling mask 200 can include air intake port 308 that can be in fluid communication with a one-way airflow valve on the interior (not shown) of the breath sampling mask 200. The breath sampling mask 200 can include one or more elastic members 202 and 204 configured to secure the breath sampling mask 200 to the patient's face. The breath sampling mask 200 can include various ports or conduits in and out of the breath sampling mask 200, some of which may be in fluid communication with valves, filters, or other components or portions of the breath sampling mask 200. By way of example, the breath sampling mask 200 can include one or more conduits 206, which can serve as a passageway for breath samples, exhaust air, wires, or the like. Like structures of breath sampling mask 200 are shown in a schematic isometric view in FIG. 13 and in a schematic top plan view in FIG. 14.

Figure 15:
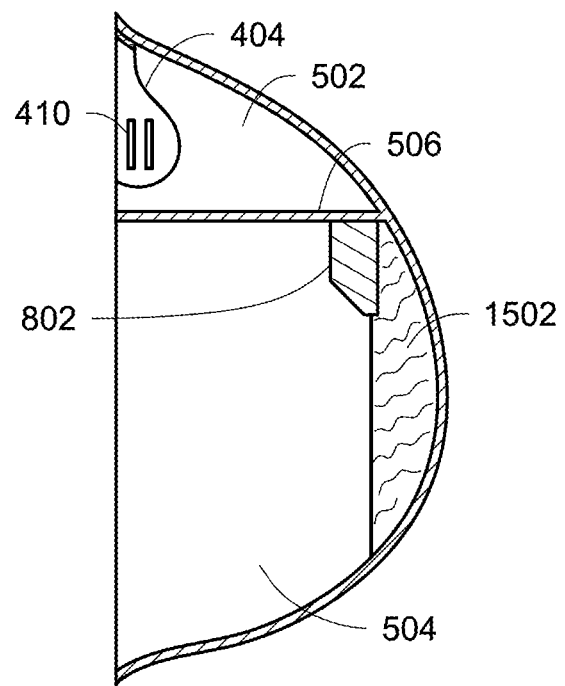
FIG. 15 is a schematic cutaway view of a breath sampling mask in accordance with various embodiments herein.

Referring now to FIG. 15, a schematic cross-sectional view of a side of the breath sampling mask 200 is shown. Breath sampling mask 200 can include nose clip member 404 attached to mask housing 402. In some embodiments, one or more sensors 410 can be connected to the nose clip member 404, the one or more sensors 410 configured to contact the skin of the patient 100 when the breath sampling mask 200 is worn by the patient 100. The sensor 410 can be selected from a group including a temperature sensor, a heart rate sensor, and a blood pressure sensor.

Breath sampling mask 200 can also include a nasal chamber 502 and a mouth chamber 504. Nasal chamber 502 and mouth chamber 504 can be separated by a dividing wall 506. It will be appreciated that in some embodiments the nasal chamber 502 defines the breath receiving chamber, while in other embodiments the mouth chamber can define the breath receiving chamber. In some embodiments, both the nasal chamber 502 and the mouth chamber can define the breath receiving chamber. In some embodiments, breath sampling mask 200 does not have a dividing wall 506. Mouth chamber 504 can include a dividing member 1502 that can span at least a portion of mouth chamber 504 without completely dividing mouth chamber 504 into more than one section. Attached to dividing member 1502 can be a chemical sensor holder 802. Chemical sensor holder 802 can serve as an anchor point to secure a chemical sensor element (not shown) within the interior, or patient-facing side, of breath sampling mask 200.

Figure 16:
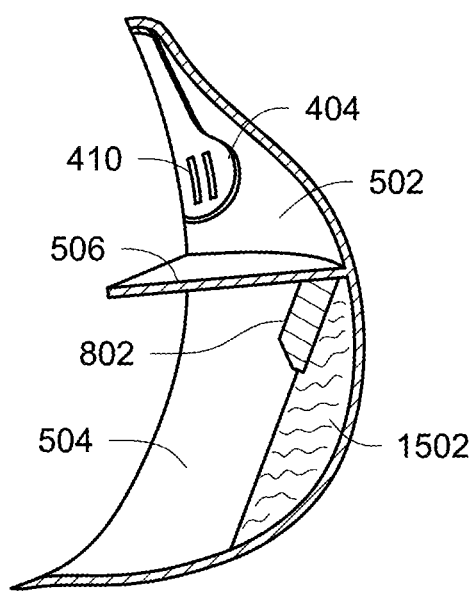
FIG. 16 is a schematic isometric view of a breath sampling mask in accordance with various embodiments herein.
Figure 17:
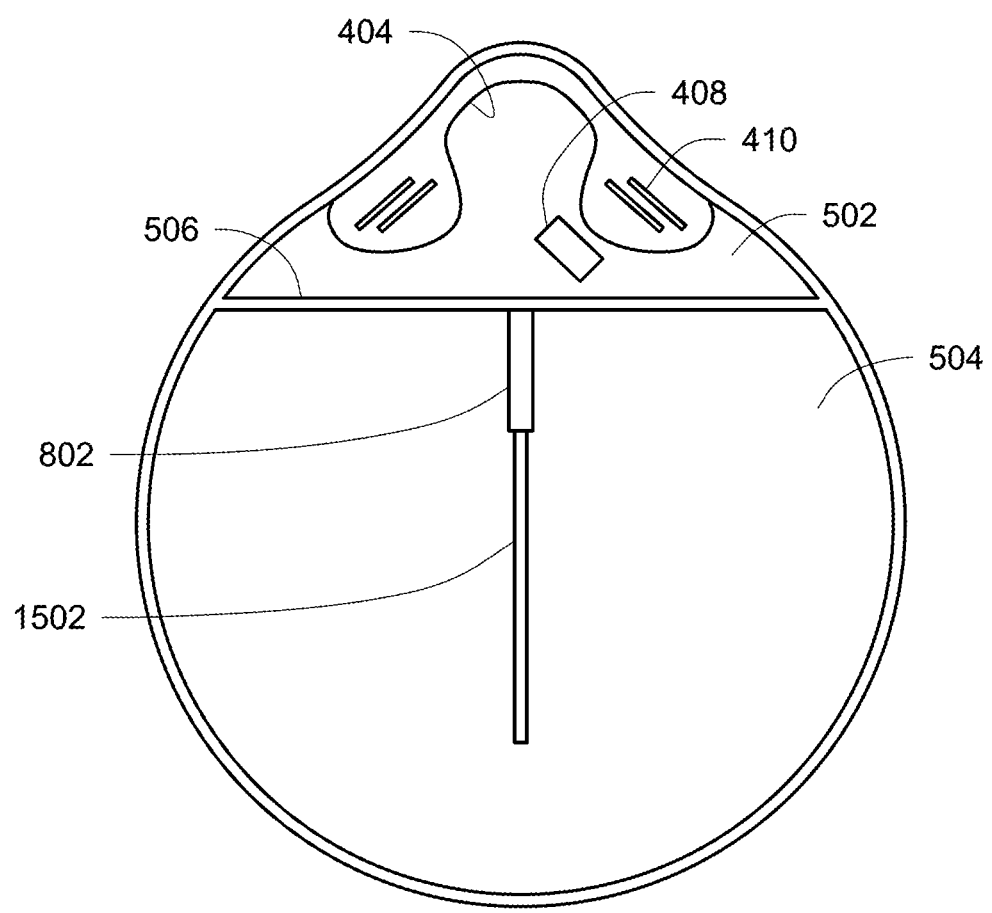
FIG. 17 a schematic bottom plan view of a breath sampling mask in accordance with various embodiments herein.

Like structures of breath sampling mask 200 are shown in a schematic isometric view in FIG. 16 and in a schematic bottom plan view in FIG. 17. FIG. 17 further shows that breath sampling mask 200 can include a one-way airflow valve 408 that can be in fluid communication with a one-way airflow valve on the exterior (not shown) of the breath sampling mask 200.

Figure 18:
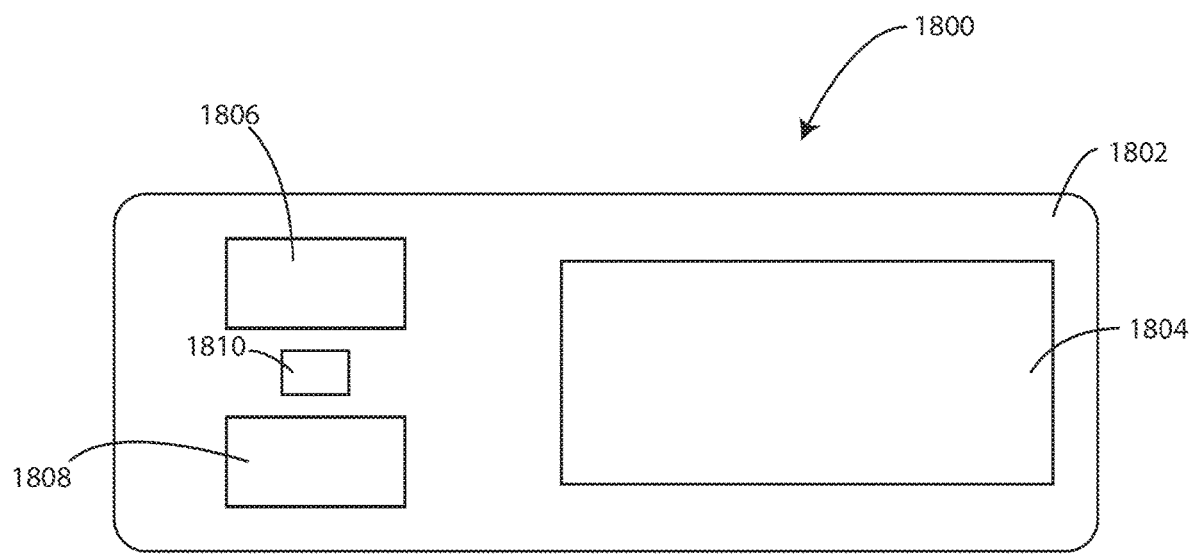
FIG. 18 a schematic top plan view of a chemical sensor element in accordance with various embodiments herein.

Referring now to FIG. 18, a schematic top plan view of a chemical sensor element 1800 is shown in accordance with various embodiments herein. The chemical sensor element 1800 can include a substrate 1802. It will be appreciated that the substrate can be formed from many different materials. By way of example, the substrate can be formed from polymers, metals, glasses, ceramics, cellulosic materials, composites, metal oxides, and the like. The thickness of the substrate can vary. In some embodiments, the substrate has sufficient structural integrity to be handled without undue flexure that could damage components thereon. In some embodiments, the substrate can have a thickness of about 0.05 mm to about 5 mm. The length and width of the substrate can also vary. In some embodiments, the length (or major axis) can be from about 0.2 cm to about 10 cm. In some embodiments, the width (perpendicular to the major axis) can be from about 0.2 cm to about 8 cm. In some embodiments, the chemical sensor element can be disposable. In some embodiments, the chemical sensor element can be reusable.

The chemical sensor element can include a first measurement zone 1804 disposed on the substrate 1802. In some embodiments, the first measurement zone 1804 can define a portion of a first gas flow path. The first measurement zone (or breath sample zone) 1804 can include a plurality of discrete binding detectors that can sense analytes in a gaseous sample, such as a breath sample. A second measurement zone (or environment sample zone) 1806, separate from the first measurement zone 1804, can also be disposed on the substrate 1802. The second measurement zone 1806 can also include a plurality of discrete binding detectors. In some embodiments, the second measurement zone 1806 can include the same (in type and/or number) discrete binding detectors that are within the first measurement zone 1804. In some embodiments, the second measurement zone 1806 can include only a subset of the discrete binding detectors that are within the first measurement zone 1804. In operation, the data gathered from the first measurement zone, which can be reflective of the gaseous sample analyzed, can be corrected or normalized based on the data gathered from the second measurement zone, which can be reflective of analytes present in the environment. However, in some embodiments, both a first and second measurement zone can reflect the breath sample analyzed. In some embodiments, a second measurement zone is not included.

In some embodiments, a third measurement zone (drift control or witness zone) 1808 can also be disposed on the substrate. The third measurement zone 1808 can include a plurality of discrete binding detectors. In some embodiments, the third measurement zone 1808 can include the same (in type and/or number) discrete binding detectors that are within the first measurement zone 1804. In some embodiments, the third measurement zone 1808 can include only a subset of the discrete binding detectors that are within the first measurement zone 1804. In some embodiments, the third measurement zone 1808 can include discrete binding detectors that are different than those of the first measurement zone 1804 and the second measurement zone 1806. In some embodiments, a third measurement zone 1808 is not included. Aspects of the third measurement zone are described in greater detail below.

The first measurement zone, the second measurement zone, and the third measurement zone can be the same size or can be of different sizes. In some embodiments, the chemical sensor element 1800 can also include a component 1810 to store reference data. The component 1810 to store reference data can be an electronic data storage device, an optical data storage device, a printed data storage device (such as a printed code), or the like. The reference data can include, but is not limited to, data regarding the third measurement zone.

In some embodiments, chemical sensor elements embodied herein can include electrical contacts (not shown) that can be used to provide power to components on the chemical sensor element 1800 and/or can be used to read data regarding the measurement zones and/or data from the stored in component 1810. However, in other embodiments there are no external electrical contacts on the chemical sensor element 1800.

Chemical sensor element 1800 can be configured to fit within chemical sensor holder 802, shown in FIGS. 8-10 and 15-17. Further aspects of exemplary chemical sensor elements can be found in U.S. application Ser. No. 14/883,895, the content of which is herein incorporated by reference in its entirety.

Many different types of circuits can be used to gather data from chemical sensor elements. It will be appreciated that the chemical sensor elements embodied herein can include those that are compatible with passive wireless sensing techniques. One example of a passive sensor circuit 2202 and a portion of a reading circuit 2222 is illustrated schematically in FIG. 22 and discussed in more detail below, however, many other circuits are contemplated herein.

Figure 19:
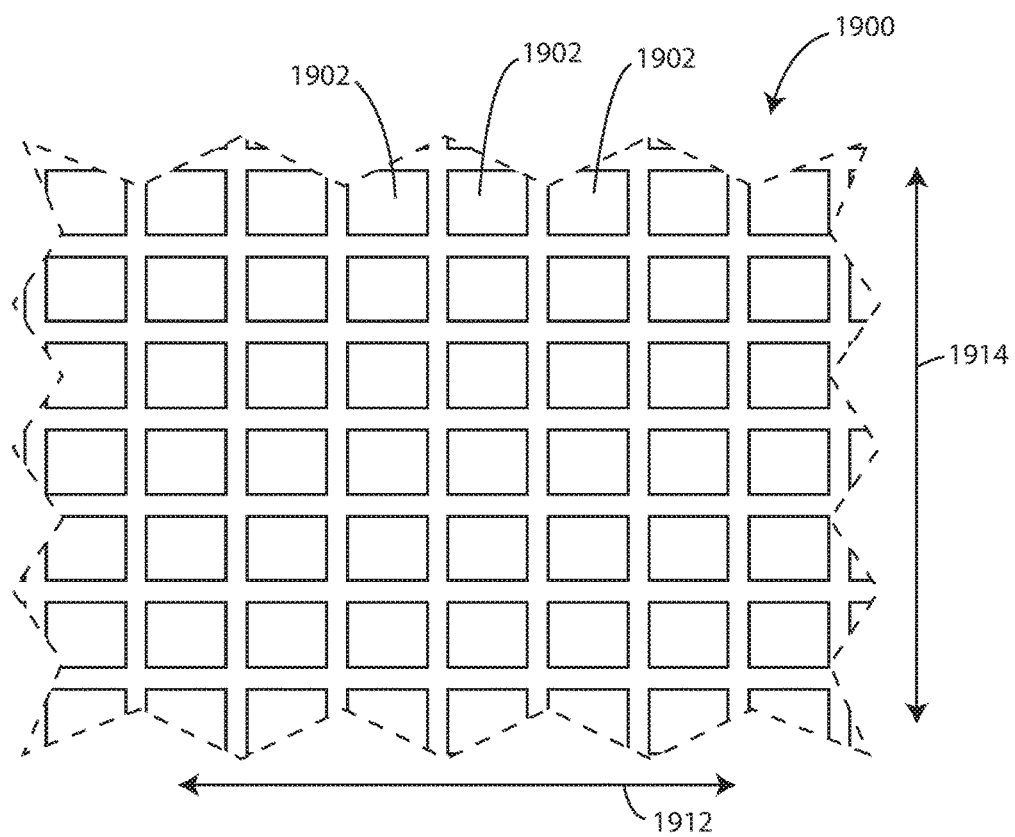
FIG. 19 is a schematic diagram of a portion of a measurement zone in accordance with various embodiments herein.

Referring now to FIG. 19, a schematic diagram of a portion of a measurement zone 1900 is shown in accordance with various embodiments herein. A plurality of discrete binding detectors 1902 can be disposed within the measurement zone 1900 in an array. In some embodiments, a chemical sensor element can include a plurality of discrete binding detectors configured in an array within a measurement zone. In some embodiments, the plurality of discrete binding detectors can be identical, while in other embodiments the plurality of discrete binding detectors can be different from one another.

In some embodiments, the discrete binding detectors can be heterogeneous in that they are all different from one another in terms of their binding behavior or specificity with regard a particular analyte. In some embodiments, some discrete binding detectors can be duplicated for validation purposes, but are otherwise heterogeneous from other discrete binding detectors. Yet in other embodiments, the discrete binding detectors can be homogeneous. While the discrete binding detectors 1902 of FIG. 19 are shown as boxes organized into a grid, it will be appreciated that the discrete binding detectors can take on many different shapes (including, but not limited to, various polygons, circles, ovals, irregular shapes, and the like) and, in turn, the groups of discrete binding detectors can be arranged into many different patterns (including, but not limited to, star patterns, zig-zag patterns, radial patterns, symbolic patterns, and the like).

In some embodiments, the order of specific discrete binding detectors 1902 across the length 1912 and width 1914 of the measurement zone can be substantially random. In other embodiments, the order can be specific. For example, in some embodiments, a measurement zone can be ordered so that the specific discrete binding detectors 1902 for analytes having a lower molecular weight are located farther away from the incoming gas flow relative to specific discrete binding detectors 1902 for analytes having a higher molecular weight which are located closer to the incoming gas flow. As such, chromatographic effects which may serve to provide separation between chemical compounds of different molecular weight can be taken advantage of to provide for optimal binding of chemical compounds to corresponding discrete binding detectors.

The number of discrete binding detectors within a particular measurement zone can be from about 1 to about 100,000. In some embodiments, the number of discrete binding detectors can be from about 1 to about 10,000. In some embodiments, the number of discrete binding detectors can be from about 1 to about 1,000. In some embodiments, the number of discrete binding detectors can be from about 2 to about 500. In some embodiments, the number of discrete binding detectors can be from about 10 to about 500. In some embodiments, the number of discrete binding detectors can be from about 50 to about 500. In some embodiments, the number of discrete binding detectors can be from about 1 to about 250. In some embodiments, the number of discrete binding detectors can be from about 1 to about 50.

Each of the discrete binding detectors suitable for use herein can include at least a portion of one or more electrical circuits. By way of example, in some embodiments, each of the discrete binding detectors can include one or more passive electrical circuits. In some embodiments, the graphene varactors can be included such that they are integrated directly on an electronic circuit. In some embodiments, the graphene varactors can be included such that they are wafer bonded to the circuit. In some embodiments, the graphene varactors can include integrated readout electronics, such as a readout integrated circuit (ROIC). The electrical properties of the electrical circuit, including resistance or capacitance, can change upon binding, such as specific and/or non-specific binding, with a component from a breath sample.

Figure 20:
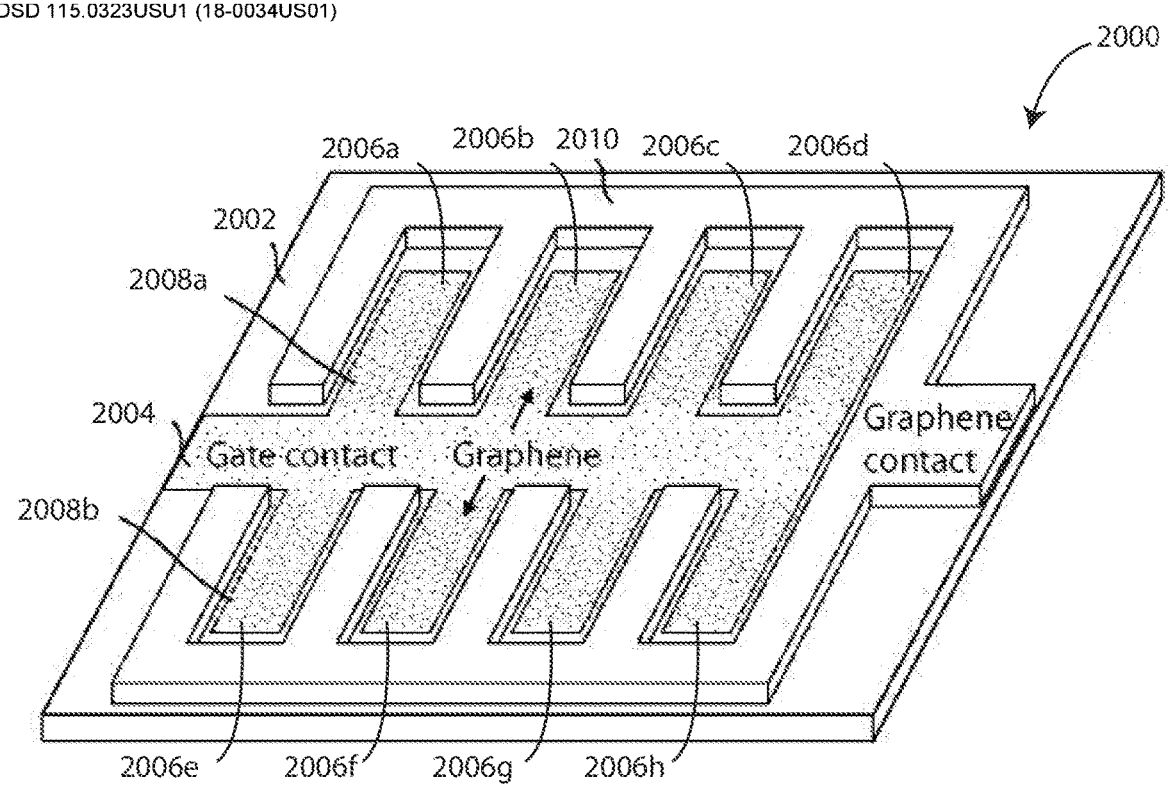
FIG. 20 is a schematic perspective view of a graphene varactor in accordance with various embodiments herein.

In some embodiments, the discrete binding detectors embodied herein can include graphene-based variable capacitors (or graphene varactors). Referring now to FIG. 20, a schematic view of a graphene varactor 2000 is shown in accordance with the embodiments herein. It will be appreciated that graphene varactors can be prepared in various ways with various geometries, and that the graphene varactor shown in FIG. 20 is just one example in accordance with the embodiments herein.

Graphene varactor 2000 can include an insulator layer 2002, a gate electrode 2004 (or "gate contact"), a dielectric layer (not shown in FIG. 20), one or more graphene layers, such as graphene layers 2008a and 2008b, and a contact electrode 2010 (or "graphene contact"). In some embodiments, the graphene layer(s) 2008a-b can be contiguous, while in other embodiments the graphene layer(s) 2008a-b can be non-contiguous. Gate electrode 2004 can be deposited within one or more depressions formed in insulator layer 2002. Insulator layer 2002 can be formed from an insulative material such as silicon dioxide, formed on a silicon substrate (wafer), and the like. Gate electrode 2004 can be formed by an electrically conductive material such as chromium, copper, gold, silver, tungsten, aluminum, titanium, palladium, platinum, iridium, and any combinations or alloys thereof, which can be deposited on top of or embedded within the insulator layer 2002. The dielectric layer can be disposed on a surface of the insulator layer 2002 and the gate electrode 2004. The graphene layer(s) 2008a-b can be disposed on the dielectric layer. The dielectric layer will be discussed in more detail below in reference to FIG. 21.

Graphene varactor 2000 includes eight gate electrode fingers 2006a-2006h. It will be appreciated that while graphene varactor 2000 shows eight gate electrode fingers 2006a-2006h, any number of gate electrode finger configurations can be contemplated. In some embodiments, an individual graphene varactor can include fewer than eight gate electrode fingers. In some embodiments, an individual graphene varactor can include more than eight gate electrode fingers. In other embodiments, an individual graphene varactor can include two gate electrode fingers. In some embodiments, an individual graphene varactor can include 1, 2, 3, 4, 5, 6, 7, 8, 9, 10, or more gate electrode fingers.

Graphene varactor 2000 can include one or more contact electrodes 2010 disposed on portions of the graphene layers 2008a and 2008b. Contact electrode 2010 can be formed from an electrically conductive material such as chromium, copper, gold, silver, tungsten, aluminum, titanium, palladium, platinum, iridium, and any combinations or alloys thereof. Further aspects of exemplary graphene varactors can be found in U.S. Pat. No. 9,513,244, the content of which is herein incorporated by reference in its entirety.

Figure 21:
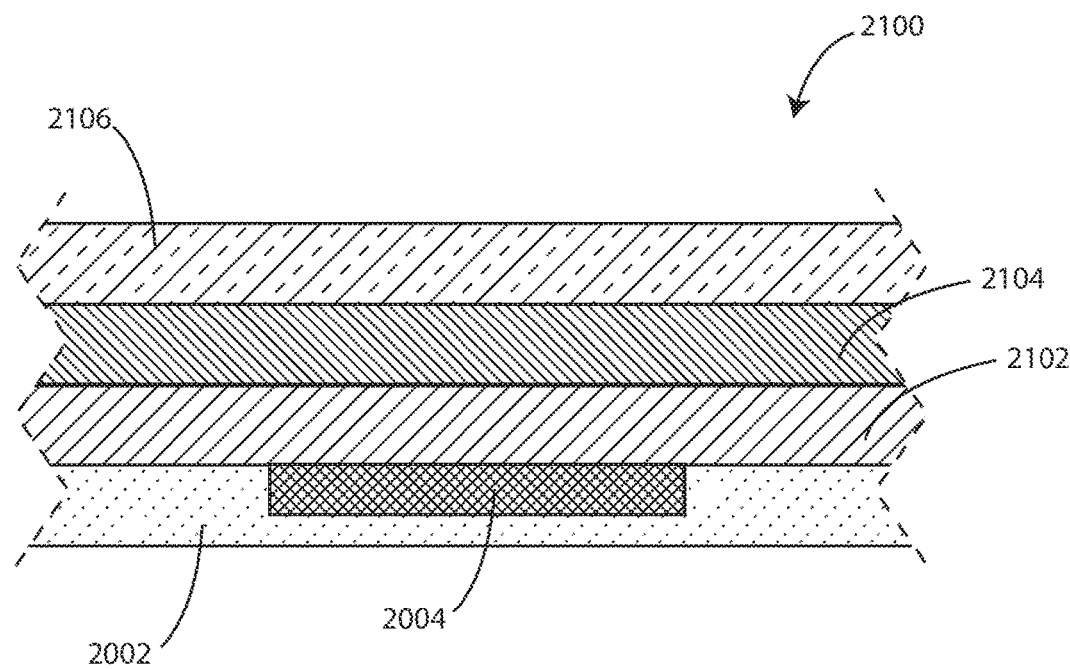
FIG. 21 is a schematic cross-sectional view of a portion of a graphene varactor in accordance with various embodiments herein.

Referring now to FIG. 21, a schematic cross-sectional view of a portion of a graphene varactor 2100 is shown in accordance with various embodiments herein. The graphene varactor 2100 can include an insulator layer 2002 and a gate electrode 2004 recessed into the insulator layer 2002. The gate electrode 2004 can be formed by depositing an electrically conductive material in the depression in the insulator layer 2002, as discussed above in reference to FIG. 20. A dielectric layer 2102 can be formed on a surface of the insulator layer 2002 and the gate electrode 2004. In some examples, the dielectric layer 2102 can be formed of a material, such as, silicon dioxide, aluminum oxide, hafnium dioxide, zirconium dioxide, hafnium silicate, or zirconium silicate.

The graphene varactor 2100 can include a single graphene layer 2104 that can be disposed on a surface of the dielectric layer 2102. The graphene layer 2104 can be surface-modified with a modification layer 2106. It will be appreciated that in some embodiments, the graphene layer 2104 is not surface-modified.

Figure 22:
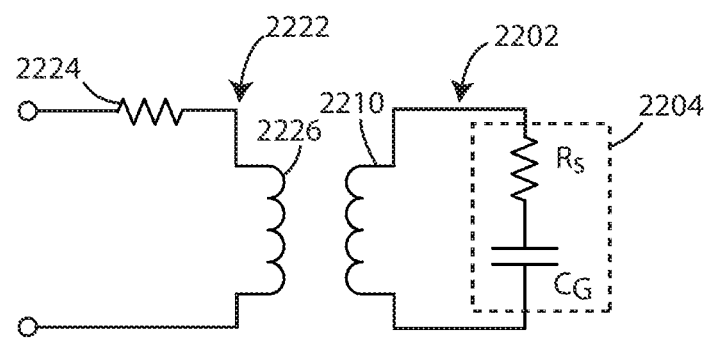
FIG. 22 is a circuit diagram of a passive sensor circuit and a portion of a reading circuit is shown in accordance with various embodiments herein.

The breath sensing systems described herein can include circuitry for generating signals from the discrete binding detectors. Such circuitry can include active and passive sensing circuits. Such circuitry can implement wired (direct electrical contact) or wireless sensing techniques. Referring now to FIG. 22, a schematic diagram of a passive sensor circuit 2202 and a portion of a reading circuit 2222 is shown in accordance with various aspects herein. In some embodiments, the passive sensor circuit 2202 can include a metal-oxide-graphene varactor 2204 (wherein RS represents the series resistance and CG represents the varactor capacitor) coupled to an inductor 2210. In some embodiments, the reading circuit 2222 can include a reading coil having a resistance 2224 and an inductance 2226. However, it will be appreciated that the circuits shown in FIG. 22 are merely one approach. Many different approaches are contemplated herein.

In some embodiments, a method of determining the presence of one or more disease states in a patient is included. The method can include putting a breath sampling mask on a patient and alerting the patient to breathe in and out to generate a breath sample. The method can include contacting the breath sample with a chemical sensor element. The method can further include collecting data from chemical sensor element comprising a plurality of discrete binding detectors. The method can further include using a measurement circuit to generate signals from the discrete binding detectors. The method can further include evaluating the signals by comparing them to previously obtained sets of signals or signal patterns.

In some embodiments, the method can include alerting the patient to breathe in through the nose and out through the mouth to generate a breath sample. In some embodiments, the method can include instructing the patient to breathe in through the mouth and out through the mouth. In some embodiments, the method can include instructing the patient to breathe in through the mouth and out through the nose. In yet other embodiments, the method can include instructing the patient to breathe in through the nose and out through the nose.

In some embodiments, the method can include evaluating the signals by comparing them to previously obtained sets of signals or patterns for patients in a non-diseased or diseased state. In some embodiments, the diseased state can include, but not be limited to cancer, including lung cancer, bloodborne cancers, prostate cancer, rectal cancer, breast cancer, liver cancer, pancreatic cancer, chronic obstructive pulmonary disease, diabetes, heart failure, and the like. In some embodiments, the comparison can include detecting patterns of differentiation between non-diseased and diseased states. In some embodiments, the method can include detecting one or more volatile organic compounds in the breath of a patient.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration to. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this technology pertains. All publications and patent applications are herein incorporated by reference to the same extent as if each individual publication or patent application was specifically and individually indicated by reference. The publications and patents disclosed herein are provided solely for their disclosure. Nothing herein is to be construed as an admission that the inventors are not entitled to antedate any publication and/or patent, including any publication and/or patent cited herein.

The technology has been described with reference to various specific and preferred embodiments and techniques. However, it should be understood that many variations and modifications may be made while remaining within the spirit and scope of the technology. As such, the embodiments of the present technology described herein are not intended to be exhaustive or to limit the technology to the precise forms disclosed in the following detailed description. Rather, the embodiments are chosen and described so that others skilled in the art can appreciate and understand the principles and practices of the present technology.

The invention claimed is:

1. A breath sensing system comprising:
   a breath sampling mask comprising
      a mask housing configured to cover a portion of a face of a patient, the mask housing defining a breath receiving chamber;
   a chemical sensor element in fluid communication with the breath sampling mask, the chemical sensor element comprising a plurality of discrete binding detectors; each binding detector comprising a graphene varactor, wherein the chemical sensor element interfaces with a breath sample collected through the breath sampling mask;
   a nose clip member for helping to secure the breath sampling mask to the face of a patient, wherein the nose clip member further comprises a sensor.

2. The breath sensing system of claim 1, further comprising circuitry for generating signals from the discrete binding detectors.

3. The breath sensing system of claim 1, the sensor comprising one or more of a temperature sensor, a heart rate sensor, and a blood pressure sensor.

4. The breath sensing system of claim 1, further comprising a second sensor comprising one or more of an ambient temperature sensor, an ambient humidity sensor, an internal temperature sensor, and an internal humidity sensor.

5. The breath sensing system of claim 1, further comprising a removable breath sample container disposed within the breath receiving chamber.

6. The breath sensing system of claim 1, further comprising a gas outflow conduit in fluid communication with the breath receiving chamber.

7. The breath sensing system of claim 1, further comprising a chemical sensor holder configured to allow removable mounting of a chemical sensor element.

8. The breath sensing system of claim 7, wherein the chemical sensor holder is disposed within the breath receiving chamber.

9. The breath sensing system of claim 1, further comprising a chemical sensor holder housing in fluid communication with the breath receiving chamber; wherein the chemical sensor element is disposed within the chemical sensor holder housing.

10. The breath sensing system of claim 1, further comprising a filter in fluid communication with a one-way airflow valve.

11. The breath sensing system of claim 1, the mask housing further comprising a dividing wall isolating the breath receiving chamber into a nasal chamber and a mouth chamber.

12. The breath sensing system of claim 11, further comprising a one-way airflow valve in fluid communication with the nasal chamber and an area outside of the mask housing, the one-way airflow valve only allowing a flow of air from the area outside of the mask housing into the nasal chamber.

13. The breath sensing system of claim 1, the graphene varactor comprising an insulator layer, a gate electrode, a dielectric layer a graphene layer, and a contact electrode.

14. The breath sensing system of claim 13, the graphene varactor comprising eight gate electrode fingers.

* * * * *